United States Patent
Saito et al.

(10) Patent No.: US 11,769,784 B2
(45) Date of Patent: *Sep. 26, 2023

(54) IMAGING DEVICE, ELECTRONIC APPARATUS, AND METHOD OF MANUFACTURING IMAGING DEVICE

(71) Applicant: SONY SEMICONDUCTOR SOLUTIONS CORPORATION, Kanagawa (JP)

(72) Inventors: Suguru Saito, Kanagawa (JP); Nobutoshi Fujii, Kanagawa (JP)

(73) Assignee: SONY SEMICONDUCTOR SOLUTIONS CORPORATION, Kanagawa (JP)

( * ) Notice: Subject to any disclaimer, the term of this patent is extended or adjusted under 35 U.S.C. 154(b) by 0 days.

This patent is subject to a terminal disclaimer.

(21) Appl. No.: 17/716,225

(22) Filed: Apr. 8, 2022

(65) Prior Publication Data

US 2022/0375984 A1 Nov. 24, 2022

Related U.S. Application Data

(63) Continuation of application No. 16/481,858, filed as application No. PCT/JP2018/004287 on Feb. 8, 2018, now Pat. No. 11,322,538.

(30) Foreign Application Priority Data

Feb. 22, 2017 (JP) .................................. 2017-030741

(51) Int. Cl.
*H01L 27/146* (2006.01)
*H01L 23/00* (2006.01)
(Continued)

(52) U.S. Cl.
CPC .......... *H01L 27/14687* (2013.01); *A61B 1/04* (2013.01); *H01L 24/14* (2013.01);
(Continued)

(58) Field of Classification Search
CPC ........... H01L 27/14687; H01L 27/1469; H01L 27/14636; H01L 27/14632;
(Continued)

(56) References Cited

U.S. PATENT DOCUMENTS

2008/0135967 A1 6/2008 Kitagawa et al.
2010/0187697 A1 7/2010 Tsai et al.
(Continued)

FOREIGN PATENT DOCUMENTS

CN 102376726 A 3/2012
CN 102569313 A 7/2012
(Continued)

OTHER PUBLICATIONS

International Search Report and Written Opinion of PCT Application No. PCT/JP2018/004287, dated Apr. 24, 2018, 09 pages of English Translation and 08 pages of ISRWO.
(Continued)

*Primary Examiner* — Vongsavanh Sengdara
(74) *Attorney, Agent, or Firm* — CHIP LAW GROUP

(57) ABSTRACT

The present technology relates to an imaging device, an electronic apparatus, and a method of manufacturing an imaging device capable of thinning a semiconductor on a terminal extraction surface while maintaining a strength of a semiconductor chip. There is provided an imaging device including: a first substrate having a pixel region in which pixels are two-dimensionally arranged, the pixels performing photoelectric conversion of light; and a second substrate in which a through silicon via is formed, in which a dug portion is formed in a back surface of the second substrate
(Continued)

opposite to an incident side of light of the second substrate, and a redistribution layer (RDL) connected to a back surface of the first substrate is formed in the dug portion. The present technology can be applied to, for example, a semiconductor package including a semiconductor chip.

13 Claims, 18 Drawing Sheets

(51) Int. Cl.
    *H01L 31/18*     (2006.01)
    *A61B 1/04*     (2006.01)

(52) U.S. Cl.
    CPC .... *H01L 27/1469* (2013.01); *H01L 27/14634* (2013.01); *H01L 27/14636* (2013.01); *H01L 31/18* (2013.01)

(58) Field of Classification Search
    CPC ........... H01L 27/14634; H01L 29/0657; H01L 23/12; H01L 24/14; H01L 31/18; H04N 25/70; A61B 1/04
    See application file for complete search history.

(56) References Cited

U.S. PATENT DOCUMENTS

| | | | |
|---|---|---|---|
| 2013/0070131 A1 | 3/2013 | Ohkubo | |
| 2013/0119501 A1 | 5/2013 | Yoshida | |
| 2013/0314573 A1 | 11/2013 | Tsukimura | |
| 2014/0070353 A1* | 3/2014 | Kim | H01L 31/18 257/459 |
| 2015/0255499 A1* | 9/2015 | Lee | H01L 24/05 257/432 |
| 2016/0172406 A1* | 6/2016 | Kawano | H01L 27/14632 257/773 |
| 2016/0181212 A1* | 6/2016 | Liu | H01L 24/32 257/621 |
| 2016/0218082 A1* | 7/2016 | Lee | H01L 21/7684 |
| 2016/0355393 A1* | 12/2016 | Liu | B81B 3/0081 |
| 2017/0018590 A1* | 1/2017 | Yiu | H01L 24/19 |
| 2017/0098678 A1* | 4/2017 | Lai | H01L 27/14636 |
| 2017/0207170 A1* | 7/2017 | Nair | H01L 21/4853 |
| 2017/0256496 A1* | 9/2017 | Lin | H01L 24/02 |
| 2017/0330871 A1* | 11/2017 | Kuan | H01L 25/167 |
| 2018/0102321 A1* | 4/2018 | Ho | H01L 24/05 |
| 2018/0204866 A1* | 7/2018 | Hsieh | H01L 27/14687 |

FOREIGN PATENT DOCUMENTS

| | | | |
|---|---|---|---|
| CN | 105702692 A | 6/2016 | |
| EP | 2592654 A1 | 5/2013 | |
| JP | 2008-130768 A | 6/2008 | |
| JP | 2010-021451 A | 1/2010 | |
| JP | 2012-015470 A | 1/2012 | |
| JP | 2016-111285 A | 6/2016 | |
| JP | 2017-022253 A | 1/2017 | |
| KR | 10-2016-0070684 A | 6/2016 | |
| TW | 201622123 A | 6/2016 | |
| WO | 2012/005075 A1 | 1/2012 | |
| WO | 2017/010263 A1 | 1/2017 | |
| WO | WO-2017018216 A1 | 2/2017 | |

OTHER PUBLICATIONS

Notice of Allowance for U.S. Appl. No. 16/481,858, dated Jan. 7, 2022, 08 pages.

Non-Final Office Action for U.S. Appl. No. 16/481,858, dated Aug. 23, 2021, 10 pages.

Non-Final Office Action for U.S. Appl. No. 16/481,858, dated Sep. 25, 2020, 08 pages.

Final Office Action for U.S. Appl. No. 16/481,858, dated Mar. 30, 2021, 14 pages.

Advisory Action for U.S. Appl. No. 16/481,858, dated Jun. 7, 2021, 02 pages.

International Preliminary Report on Patentability of PCT Application No. PCT/JP2018/004287, dated Sep. 6, 2019, 10 pages of English Translation and 05 pages of IPRP.

* cited by examiner

IMAGING DEVICE, ELECTRONIC APPARATUS, AND METHOD OF MANUFACTURING IMAGING DEVICE

CROSS REFERENCE TO RELATED APPLICATIONS

The present application is a continuation application of U.S. patent application Ser. No. 16/481,858, filed on Jul. 30, 2019, which is a U.S. National Stage Entry of International Patent Application No. PCT/JP2018/004287 filed on Feb. 8, 2018, which claims priority benefit of Japanese Patent Application No. JP 2017-030741 filed in the Japan Patent Office on Feb. 22, 2017. Each of the above-referenced applications is hereby incorporated herein by reference in its entirety.

TECHNICAL FIELD

The present technology relates to an imaging device, an electronic apparatus, and a method of manufacturing an imaging device, and in particular, to an imaging device, an electronic apparatus, and a method of manufacturing an imaging device capable of thinning a semiconductor on a terminal extraction surface while maintaining a strength of a semiconductor chip.

BACKGROUND ART

A wafer level chip size package (WCSP) in which a semiconductor device (semiconductor package) is downsized to a chip size has been known (see, for example, Patent Document 1).

CITATION LIST

Patent Document

Patent Document 1: Japanese Patent Application Laid-Open No. 2010-21451

SUMMARY OF THE INVENTION

Problems to be Solved by the Invention

By the way, in a semiconductor package including a wafer level chip size package (WCSP) having a backside redistribution (RDL) electrode structure, there is a demand to reduce a thickness of the semiconductor package by reducing a film thickness of silicon (Si) on a terminal extraction surface of a backside.

However, when the film thickness of silicon (Si) on the terminal extraction surface is reduced, there is a possibility that a strength of a semiconductor chip will be reduced. Therefore, a technology for reducing the film thickness of silicon (Si) on the terminal extraction surface while maintaining the strength of the semiconductor chip has been demanded.

The present technology has been made in view of such a situation, and can enable a semiconductor on a terminal extraction surface to be thinned while maintaining a strength of a semiconductor chip.

Solutions to Problems

An imaging device according to an aspect of the present technology is an imaging device including: a first substrate having a pixel region in which pixels are two-dimensionally arranged, the pixels performing photoelectric conversion of light; and a second substrate in which a through silicon via is formed, in which a dug portion is formed in a back surface of the second substrate opposite to an incident side of light of the second substrate, and a redistribution layer (RDL) connected to a back surface of the first substrate is formed in the dug portion.

An electronic apparatus according to an aspect of the present technology is an electronic apparatus including an imaging device, in which the imaging device includes: a first substrate having a pixel region in which pixels are two-dimensionally arranged, the pixels performing photoelectric conversion of light; and a second substrate in which a through silicon via is formed, a dug portion being formed in a back surface of the second substrate opposite to an incident side of light of the second substrate, and a redistribution layer (RDL) connected to a back surface of the first substrate being formed in the dug portion.

In the imaging device and the electronic apparatus according to an aspect of the present technology, the first substrate having the pixel region in which the pixels that perform the photoelectric conversion of the light are two-dimensionally arranged and the second substrate in which the through silicon via is formed are stacked. Then, the dug portion is formed in the back surface of the second substrate opposite to the incident side of the light of the second substrate, and the redistribution layer (RDL) connected to the back surface of the first substrate is formed in the dug portion.

A method of manufacturing an imaging device according to an aspect of the present technology is a method of manufacturing an imaging device, including: a first step of forming a dug portion in a back surface of a second substrate opposite to an incident side of light of the second substrate in which a through silicon via is formed, in a first substrate having a pixel region in which pixels are two-dimensionally arranged and the second substrate stacked on the first substrate, the pixels performing photoelectric conversion of light; and a second step of forming a redistribution layer (RDL) in the dug portion, the redistribution layer (RDL) being connected to a back surface of the first substrate.

In the method of manufacturing an imaging device according to an aspect of the present technology, in the first substrate having the pixel region in which the pixels that perform the photoelectric conversion of the light are two-dimensionally arranged and the second substrate stacked on the first substrate, the dug portion is formed in the back surface of the second substrate opposite to the incident side of the light of the second substrate in which the through silicon via is formed, and the redistribution layer (RDL) connected to the back surface of the first substrate is formed in the dug portion.

Effects of the Invention

According to an aspect of the present technology, it is possible to thin a semiconductor on a terminal extraction surface while maintaining a strength of a semiconductor chip.

Note that an effect described here is not necessarily limited, and may be any effect described in the present disclosure.

MODE FOR CARRYING OUT THE INVENTION

Hereinafter, embodiments of the present technology will be described with reference to the drawings. Note that a description will be given in the following order.
1. Outline of Present Technology
2. First Embodiment: Basic Structure
3. Second Embodiment: Structure in Case of Performing Planarization After Mounting of Solder Ball
4. Third Embodiment: Structure in Which Surfaces of Solder Mask and Solder Ball are Flush with Each Other
5. Fourth Embodiment: Structure in Which Surfaces of Frame, Solder Mask, and Solder Ball are Flush with One Another
6. Fifth Embodiment: Structure in Which Central Portion of Semiconductor Chip is Not Dug
7. Sixth Embodiment: Structure in Which Cu-LGA is Formed
8. Seventh Embodiment: Multilayer RDL Wiring Structure
9. Eighth Embodiment: Structure in Which Transparent Member Is Not Present
10. Configuration of Electronic Apparatus
11. Use Example of Imaging Device
12. Application Example to In-vivo Information Acquisition System
13. Application Example to Moving Body <1. Outline of Present Technology>

Figure 1:
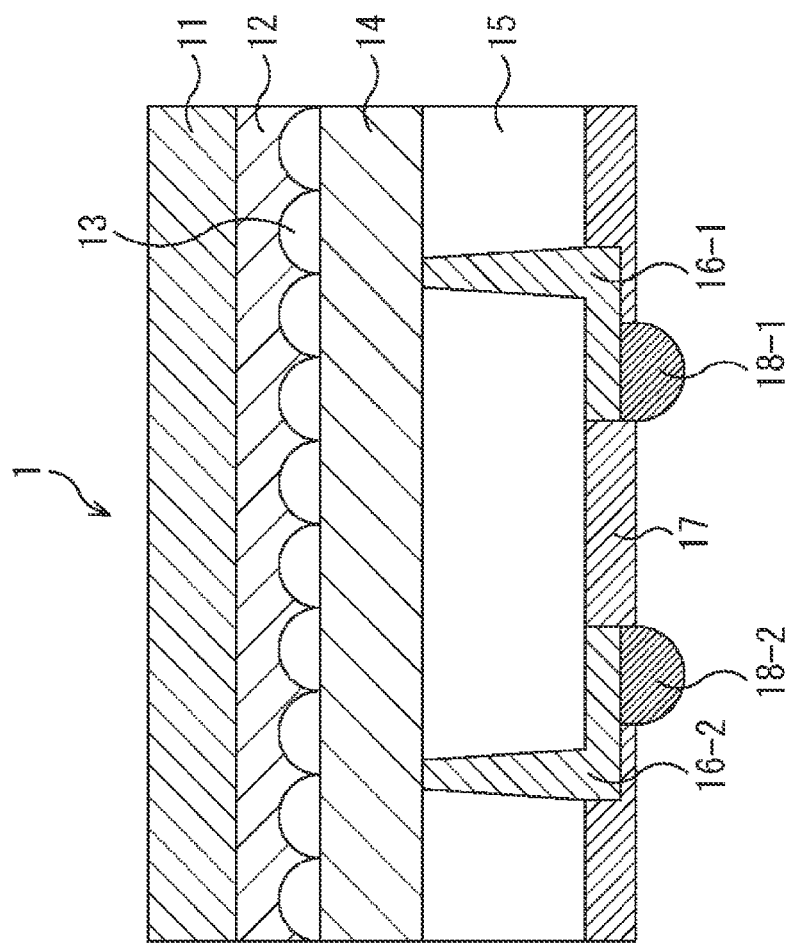
FIG. 1 is a cross-sectional view illustrating a structure of a general imaging device.

FIG. 1 is a view illustrating a structure of a general imaging device.

The general imaging device 1 is a semiconductor package configured as a wafer level chip size package (WCSP) having a backside RDL electrode structure. The imaging device 1 is configured by stacking a transparent member 11, an adhesive 12, a first substrate 14, and a second substrate 15.

Furthermore, in the general imaging device 1, a semiconductor chip includes on-chip lenses 13 formed on an upper surface (surface) of the first substrate 14 as an image sensor, and the second substrate 15 as a logic circuit.

Since the general imaging device 1 has a backside RDL electrode structure, TSV/RDL wirings 16-1 and 16-2 including through silicon vias (TSVs) penetrating through silicon (Si) of the second substrate 15 in a vertical direction and redistribution layers (RDLs) in a horizontal direction are formed and are connected to a lower surface (back surface) of the first substrate 14. Furthermore, solder balls 18-1 and 18-2 are mounted on the TSV/RDL wirings 16-1 and 16-2, and parts of the TSV/RDL wirings 16-1 and 16-2 and the solder balls 18-1 and 18-2 formed on a lower surface of the second substrate 15 are covered with a solder mask 17.

In the general imaging device 1 having such a configuration, it is required to reduce a film thickness of silicon (Si) on a terminal extraction surface due to a demand for reducing a thickness of the semiconductor package, but when the film thickness of silicon (Si) is reduced, there is a possibility that a strength of the semiconductor chip will be reduced. Therefore, a technology for reducing a film thickness of a semiconductor (silicon (Si)) on the terminal extraction surface while maintaining the strength of the semiconductor chip has been demanded.

Therefore, the present technology proposes solution means for reducing the film thickness of the semiconductor (silicon (Si)) on the terminal extraction surface while maintaining the strength of the semiconductor chip. Hereinafter, this solution means will be described by first to eighth embodiments.

<2. First Embodiment>
(First Structure)

Figure 2:
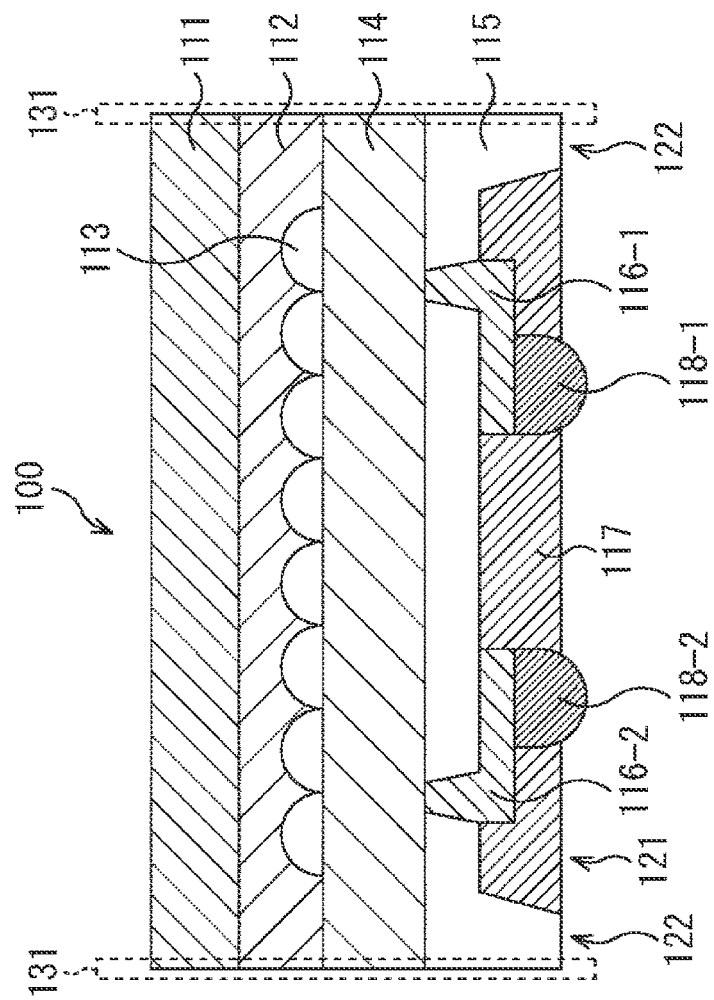
FIG. 2 is a cross-sectional view illustrating an example of a structure of an imaging device according to a first embodiment.

FIG. 2 is a cross-sectional view illustrating an example of a structure of an imaging device according to a first embodiment.

The imaging device 100 according to the first embodiment is an example of a semiconductor package configured as a WCSP having a backside RDL electrode structure.

Note that, in the following description, in the imaging device 100, a light incident surface is referred to as an upper surface (front surface), and a surface opposite to the light incident surface is referred to as a lower surface (back surface).

In FIG. 2, the imaging device 100 is configured by stacking a transparent member 111, an adhesive 112, a first substrate 114, and a second substrate 115. In other words, in the imaging device 100, a backside RDL electrode structure in which terminals of a device configured by bonding the transparent member 111 and the first substrate 114 to each other by the adhesive 112 are extruded from a lower surface side (back surface side) of the first substrate 114 is adopted.

The first substrate 114 is configured as an image sensor such as a complementary metal oxide semiconductor (CMOS) image sensor, a charge coupled device (CCD) image sensor or the like. In the first substrate 114, a photodiode formed by a PN junction is formed for each pixel. Furthermore, although not illustrated, pixel transistors such as transfer transistors, amplification transistors or the like are also formed on the first substrate 114.

On-chip lenses 113 are formed on an upper surface (front surface) of the first substrate 114. Note that although not illustrated, a color filter corresponding to a color component such as red (R), green (G), blue (B) or the like may be formed. The first substrate 114 is fixed by the transparent member 111 such as glass or the like and the adhesive 112.

The second substrate 115 is a silicon substrate including silicon (Si), and is configured as, for example, a logic circuit. For example, a semiconductor chip includes the first substrate 114 as the image sensor and the second substrate 115 as the logic circuit.

A dug portion 121 having sidewalls of a forward tapered shape is formed in a lower surface side (back surface side) of the second substrate 115. TSV/RDL wirings 116-1 and 116-2 including through silicon vias (TSVs) penetrating through silicon (Si) of the second substrate 115 in a vertical direction and redistribution layers (RDLs) in a horizontal direction are formed in the dug portion 121 and are connected to a lower surface (back surface) of the first substrate 114.

The TSV/RDL wirings 116-1 and 116-2 include, for example, copper (Cu), tungsten (W), polysilicon or the like. A solder ball 118-1 is mounted on the TSV/RDL wiring 116-1. Furthermore, a solder ball 118-2 is mounted on the TSV/RDL wiring 116-2. The solder balls 118-1 and 118-2 are provided as external terminals on a terminal extraction surface side when the imaging device 100 is mounted on an electronic apparatus or the like.

Furthermore, in the second substrate 115, a solder mask 117 is formed in a region of the dug portion 121 except for a region in which the TSV/RDL wirings 116-1 and 116-2 and the solder balls 118-1 and 118-2 mounted on the TSV/RDL wirings 116-1 and 116-2 are formed, and is formed to cover parts of the TSV/RDL wirings 116-1 and 116-2 and the solder balls 118-1 and 118-2.

Specifically, by processing silicon (Si) of the second substrate 115 to form the dug portion 121 having the sidewalls of the forward tapered shape, the region in which the TSV/RDL wirings 116-1 and 116-2 or the solder balls 118-1 and 118-2 are formed is dug. Then, if the second substrate 115 is viewed from the lower surface side (back surface side), a surface (terminal extraction surface) of silicon (Si) of the second substrate 115 has a region of a frame shape.

In this case, surfaces (surface of silicon (Si)) of a frame portion 122 and a scribe portion 131 constituting the region of the frame shape and a surface of the solder mask 117 embedded in the dug portion 121 are planarized so as to be flush with each other.

Note that a region of the scribe portion 131 is a part of the region of the frame shape, and is a "margin" provided between patterns on a wafer. In other words, in a case where the second substrate 115 is viewed from the lower surface side (back surface side), the vicinity of silicon (Si) of the second substrate 115 is the region of the scribe portion 131.

In other words, in the region of the frame shape, a region inside a scribe region is taken as a region (variable region) of the frame portion 122.

As described above, in the second substrate 115 constituting the semiconductor chip, silicon (Si) is dug to form the dug portion 121 having the sidewalls of the forward tapered shape and thus form a structure in which a film thickness of silicon (Si) in the region of the frame shape (regions of the frame portion 122 and the scribe portion 131) is not reduced.

With this arrangement, silicon (Si) has a sufficient film thickness in the region of the frame shape, that is, in the regions of the frame portion 122 and the scribe portion 131, and sufficient chip hardness can thus be secured in the semiconductor chip including the first substrate 114 (image sensor) and the second substrate 115 (logic circuit). Furthermore, since parts of the TSV/RDL wirings 116-1 and 116-2 or the solder balls 118-1 and 118-2 are formed in the dug portion 121 formed in silicon (Si) of the second substrate 115, a height of the imaging device 100 as the semiconductor package can be reduced as compared with a structure of the general imaging device 1 (FIG. 1).

As described above, in a case where the imaging device 100 according to the first embodiment has the backside RDL electrode structure, the imaging device 100 has a structure in which the dug portion 121 is formed in silicon (Si) of the second substrate 115, parts of the TSV/RDL wirings 116-1 and 116-2 and the solder balls 118-1 and 118-2 are formed in the dug portion 121, and the solder mask 117 is embedded in the dug portion 121. Since the imaging device 100 according to the first embodiment has such a structure, it is possible to reduce a height of the semiconductor package and secure a chip strength of the semiconductor chip.

That is, as compared with the structure of the general imaging device 1 (FIG. 1), in the imaging device 100 according to the first embodiment, as parts of the TSV/RDL wirings 116-1 and 116-2 and the solder balls 118-1 and 118-2 are formed in the dug portion 121, the height of the imaging device 100 can be correspondingly reduced, and since the thickness of silicon (Si) in the region of the frame portion 122 or the scribe portion 131 is sufficiently secured, the chip strength of the semiconductor chip can be maintained.

(First Manufacturing Method)

Next, a flow of processes of manufacturing the imaging device 100 according to the first embodiment will be described with reference to schematic views of FIGS. 3A, 3B, 3C, 4A, 4B, and 4C.

Note that although not illustrated, in the previous step of processes shown in FIGS. 3A, 3B, 3C, 4A, 4B, and 4C, the imaging device 100 is configured by stacking the first substrate 114 on which the transparent member 111, the adhesive 112, and the on-chip lenses 113 are formed, and the second substrate 115.

Figure 3:
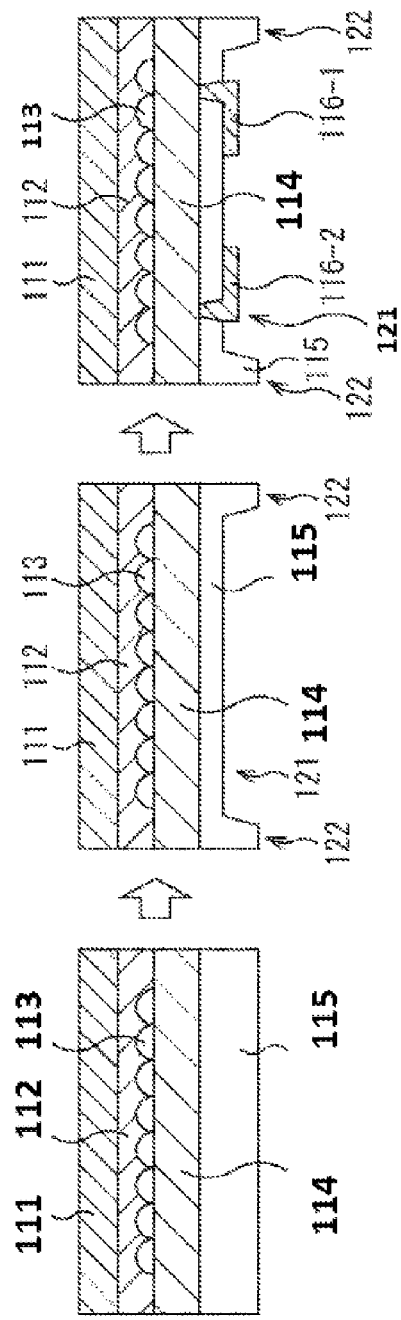
FIGS. 3A, 3B, and 3C are views for describing a flow of processes of manufacturing the imaging device according to the first embodiment.

Thereafter, in the processes of manufacturing the imaging device 100 according to the first embodiment, first, a thinning process is performed. In this thinning process, as illustrated in FIG. 3A, the film thickness of silicon (Si) of the second substrate 115 is reduced, such that a thickness of the imaging device 100 is reduced.

In this case, if the thickness of silicon (Si) of the second substrate 115 is simply reduced, the thickness of the entire imaging device 100 as the semiconductor package can be reduced, but there is a problem that a strength of the semiconductor chip is reduced by the reduction in the thickness. Therefore, in the present technology, in the thinning process, the thickness of silicon (Si) of the second substrate 115 is ensured enough to maintain the strength of the semiconductor chip.

Next, a digging process is performed. In this digging process, as illustrated in FIG. 3B, silicon (Si) after the thinning of the second substrate 115 is dug, such that the dug portion 121 is formed.

Here, when this digging process is performed, considering applying unevenness of a resist in a lithography process, which is the subsequent process, disconnection of a plating, or the like, it is preferable that the sidewalls of the dug portion 121 formed in silicon (Si) of the second substrate 115 have the forward tapered shape rather than a vertical shape.

An example of a method of performing control to form the dug portion 121 in the forward tapered shape can include alkaline anisotropic etching using a hard mask. By using this alkali anisotropic etching, a tapered shape along a face of silicon (Si) can be obtained by face orientation dependence of silicon (Si) of the second substrate 115. Furthermore, when silicon (Si) is dug, by performing alkali anisotropic etching processing, it is possible to sufficiently cope with the applying unevenness or the disconnection of the plating.

Next, a TSV/RDL forming process is performed. In this TSV/RDL forming process, as illustrated in FIG. 3C, by processing silicon (Si) of the second substrate 115 in which the dug portion 121 having the sidewalls of the forward tapered shape is formed, through silicon vias (TSVs) penetrating through silicon (Si) in the vertical direction are formed, and the TSV/RDL wirings 116-1 and 116-2 are formed.

Figure 4:
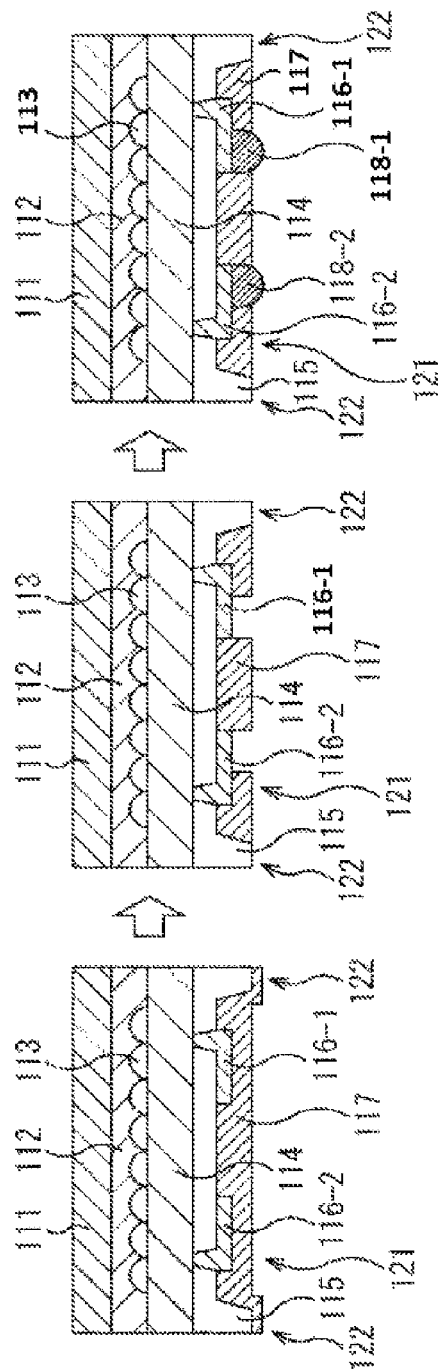
FIGS. 4A, 4B, and 4C are views for describing a flow of processes of manufacturing the imaging device according to the first embodiment.

Next, a solder mask applying process is performed. In the solder mask applying process, as illustrated in FIG. 4A, the dug portion 121 having the sidewalls of the forward tapered shape is embedded by the solder mask 117 so as to cover the TSV/RDL wirings 116-1 and 116-2 formed in silicon (Si) of the second substrate 115. Note that, here, the solder mask 117 is also applied to the region of the frame shape (the regions of the frame portion 122 and the scribe portion 131).

Next, a solder mask planarization process is performed. In this solder mask planarization process, as illustrated in FIG. 4B, planarization of the solder mask 117 applied so as to embed the dug portion 121 is performed using, for example, a grinder (grinding machine), a surface planer, chemical mechanical polishing (CMP), or the like.

Note that, in the solder mask planarization process, a surface of the solder mask 117 applied to the region of the frame shape (the regions of the frame portion 122 and the scribe portion 131) in the solder mask applying process described above may be planarized so as to be flush with a surface of silicon (Si) or the solder mask 117 of the region of the frame shape (the regions of the frame portion 122 and the scribe portion 131) may remain. In an example of FIG. 4B, the surface of the solder mask 117 applied to the region of the frame shape is planarized so as to be flush with the surface of silicon (Si).

Next, a patterning process is performed. In this patterning process, as illustrated in FIG. 4B, patterning for defining positions at which the solder balls 118-1 and 118-2 are to be mounted is performed on the solder mask 117 applied to the dug portion 121 formed in silicon (Si) of the second substrate 115. By this patterning process, portions of the TSV/RDL wirings 116-1 and 116-2 on which the solder balls 118-1 and 118-2 are mounted are exposed.

Finally, a solder ball mounting and reflow process is performed. In the solder ball mounting and reflow process, as illustrated in FIG. 4C, the solder balls 118-1 and 118-2 are mounted at the positions defined in the patterning process described above. Furthermore, after the solder balls 118-1 and 118-2 are mounted, soldering is performed in a reflow manner, such that the TSV/RDL wiring 116-1 and the solder ball 118-1 are bonded to each other and the TSV/RDL wiring 116-2 and the solder ball 118-2 are bonded to each other.

The processes of manufacturing the imaging device 100 according to the first embodiment are performed as described above.

<3. Second Embodiment>
(Second Structure)

Figure 5:
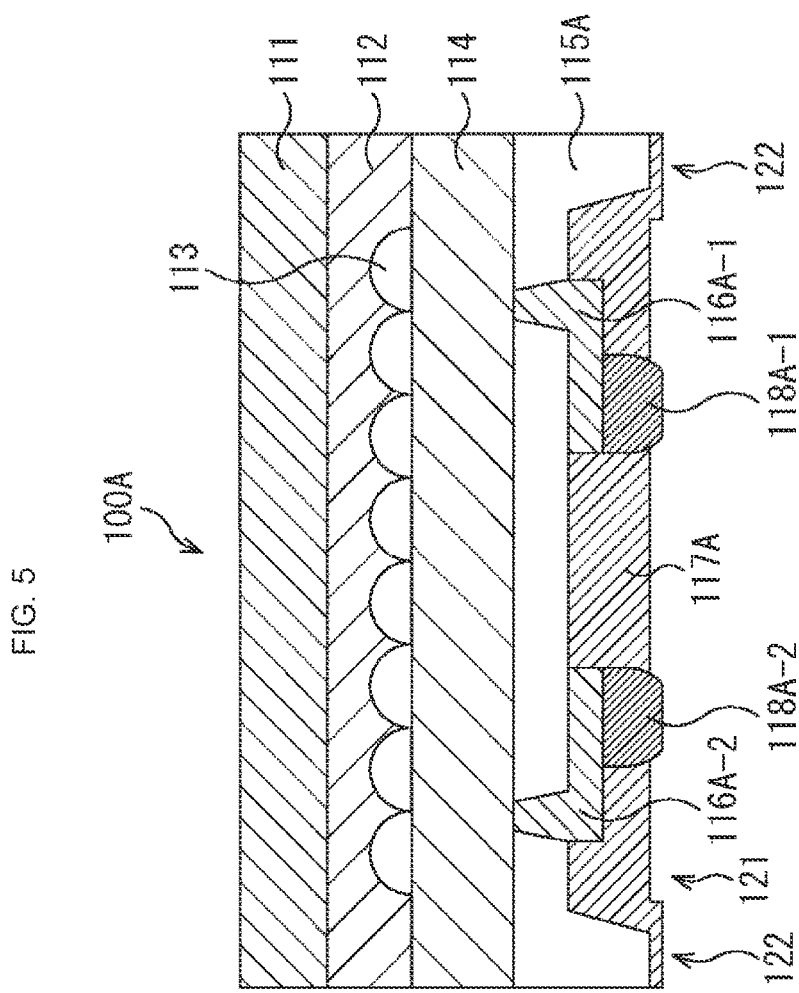
FIG. 5 is a cross-sectional view illustrating an example of a structure of an imaging device according to a second embodiment.

FIG. 5 is a cross-sectional view illustrating an example of a structure of an imaging device according to a second embodiment.

In the imaging device 100A of FIG. 5, portions that are the same as or correspond to those of the imaging device 100 of FIG. 2 will be denoted by the same or corresponding reference numerals. In other words, the imaging device 100A of FIG. 5 is different in a part of a structure of a second substrate 115A from the imaging device 100 of FIG. 2.

Specifically, in the imaging device 100A of FIG. 5, a dug portion 121 having sidewalls of a forward tapered shape is formed in silicon (Si) of the second substrate 115A, and TSV/RDL wirings 116A-1 and 116A-2 and solder balls 118A-1 and 118A-2 are formed in the dug portion 121. Furthermore, a solder mask 117A is formed in the dug portion 121 so as to cover parts of the TSV/RDL wirings 116A-1 and 116A-2 and the solder balls 118A-1 and 118A-2.

Here, as compared with the imaging device 100 of FIG. 2, in the imaging device 100A of FIG. 5, the solder mask 117A is also applied to a region of a frame shape (regions of a frame portion 122 and a scribe portion 131), and the solder balls 118A-1 and 118A-2 are planarized so as to be flush with a surface of the solder mask 117A applied to the region of the frame shape and regions of the sidewalls of the dug portion 121.

In other words, surfaces of the solder balls 118A-1 and 118A-2 that are planarized are flush with the surface of the solder mask 117A applied to the region of the frame shape (the regions of the frame portion 122 and the scribe portion 131) and the regions of the sidewalls of the dug portion 121. Note that, in the dug portion 121, the surface of the solder mask 117A in the regions of the sidewalls of the dug portion 121 and a surface of the solder mask 117A in the other regions are not flush with each other, and have a step therebetween.

As described above, the imaging device 100A of FIG. 5 is different in structures of the solder balls 118A-1 and 118A-2 and the solder mask 117A from the imaging device 100 of FIG. 2, but is the same as the imaging device 100 of FIG. 2 in that, in the second substrate 115A, silicon (Si) is dug to form the dug portion 121 having the sidewalls of the forward tapered shape and thus form a structure in which a film thickness of silicon (Si) in the region of the frame shape (the regions of the frame portion 122 and the scribe portion 131) is not reduced.

With this arrangement, silicon (Si) has a sufficient film thickness in the region of the frame shape (the regions of the frame portion 122 and the scribe portion 131), and sufficient chip hardness can thus be secured in a semiconductor chip including the first substrate 114 (image sensor) and the second substrate 115A (logic circuit). Furthermore, since parts of the TSV/RDL wirings 116A-1 and 116A-2 or the solder balls 118A-1 and 118A-2 are formed in the dug portion 121 formed in silicon (Si) of the second substrate 115A, a height of the imaging device 100A as a semiconductor package can be reduced as compared with a structure of the general imaging device 1 (FIG. 1).

As described above, in a case where the imaging device 100A according to the second embodiment has a backside RDL electrode structure, the imaging device 100A has a structure in which the dug portion 121 is formed in silicon (Si) of the second substrate 115A, parts of the TSV/RDL wirings 116A-1 and 116A-2 and the solder balls 118A-1 and 118A-2 are formed in the dug portion 121, and the solder mask 117A is embedded in the dug portion 121. Since the imaging device 100A according to the second embodiment has such a structure, it is possible to reduce a height of the semiconductor package and secure a chip strength of the semiconductor chip.

Note that, in the imaging device 100A of FIG. 5, illustration of the region of the scribe portion 131 is omitted, but the region of the scribe portion 131, which is a part of the region of the frame shape, is provided in the vicinity of silicon (Si) of the second substrate 115A, similarly to the imaging device 100 of FIG. 2. Furthermore, similarly to the second embodiment, illustration of the region of this scribe portion 131 is omitted in other embodiments as described later.

(Second Manufacturing Method)

Next, a flow of processes of manufacturing the imaging device 100A according to the second embodiment will be described with reference to schematic views of FIGS. 6A, 6B, 6C, 7A, 7B, and 7C.

Note that, in a second manufacturing method, a thinning process, a digging process, a TSV/RDL forming process, and a solder mask applying process are similar to those illustrated in the first manufacturing method (FIGS. 3A, 3B, 3C, 4A, 4B, and 4C) described above.

Figure 6:
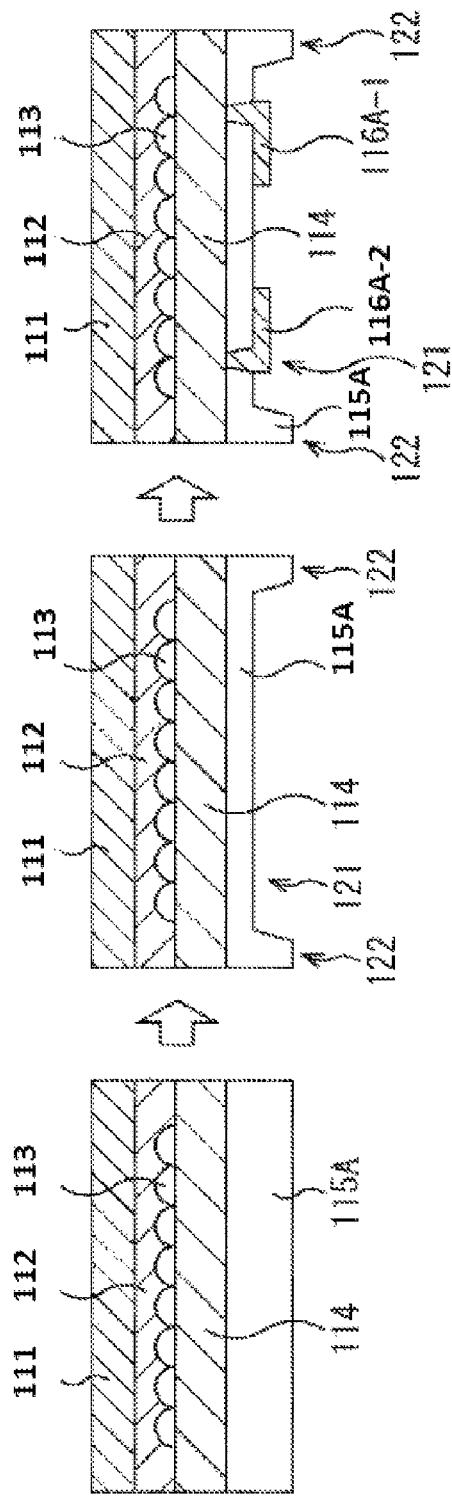
FIGS. 6A, 6B, and 6C are views for describing a flow of processes of manufacturing the imaging device according to the second embodiment.

In other words, in the thinning process, a film thickness of silicon (Si) of the second substrate 115A is reduced (FIG. 6A), and in the digging process, the dug portion 121 having the sidewalls of, for example, the forward tapered shape is formed in silicon (Si) of the second substrate 115A (FIG. 6B).

Figure 7:
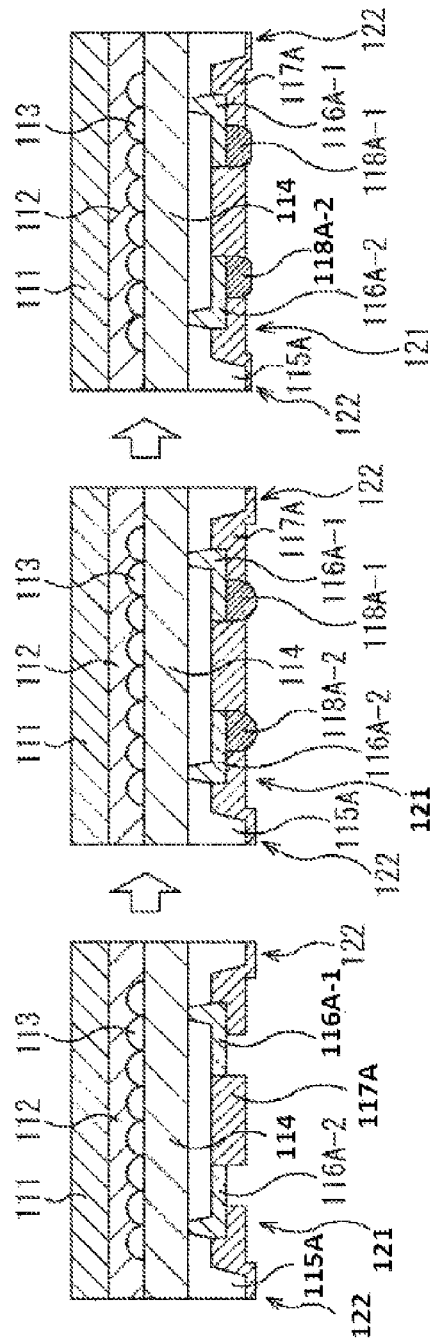
FIGS. 7A, 7B, and 7C are views for describing a flow of processes of manufacturing the imaging device according to the second embodiment.

Furthermore, in the TSV/RDL forming process, through silicon vias (TSVs) are formed in silicon (Si) of the second substrate 115A and TSV/RDL wirings 116A-1 and 116A-2 are formed (FIG. 6C) in the through silicon vias (TSVs), and in the solder mask applying process, the dug portion 121 is embedded by the solder mask 117A (FIG. 7A). Note that, here, the solder mask 117A is also applied to the region of the frame shape (the regions of the frame portion 122 and the scribe portion 131).

After the solder mask applying process, a patterning process is performed. In this patterning process, as illustrated in FIG. 7A, patterning for defining positions at which the solder balls 118A-1 and 118A-2 are to be mounted is performed on the solder mask 117A applied to the dug portion 121 formed in silicon (Si) of the second substrate 115A. By this patterning process, portions of the TSV/RDL wirings 116A-1 and 116A-2 on which the solder balls 118A-1 and 118A-2 are mounted are exposed.

Next, a solder ball mounting and reflow process is performed. In the solder ball mounting and reflow process, as illustrated in FIG. 7B, the solder balls 118A-1 and 118A-2 are mounted at the positions defined in the patterning process described above. Furthermore, after the solder balls 118A-1 and 118A-2 are mounted, soldering is performed in a reflow manner, such that the TSV/RDL wiring 116A-1 and the solder ball 118A-1 and the TSV/RDL wiring 116A-2 and the solder ball 118A-2 are bonded to each other, respectively.

Finally, a planarization process is performed. In this planarization process, as illustrated in FIG. 7C, planarization of the solder mask 117A applied so as to embed the dug portion 121 is performed, but here, planarization of the solder balls 118A-1 and 118A-2 is also performed, such that the surface of the solder mask 117A and the surfaces of the solder balls 118A-1 and 118A-2 can be flush with each other.

Note that, in the planarization process, the planarization of the solder mask 117A and the solder balls 118A-1 and 118A-2 is performed using, for example, a grinder (grinding machine), a surface planer, CMP, or the like.

Furthermore, in the planarization process, the solder mask 117A applied to the region of the frame shape (the regions of the frame portion 122 and the scribe portion 131) in the solder mask applying process described above may remain or the solder mask 117A of the region of the frame shape (the regions of the frame portion 122 and the scribe portion 131) may be planarized so as to be flush with a surface of silicon (Si). In an example of FIG. 7C, the solder mask 117A applied to the region of the frame shape remains.

The processes of manufacturing the imaging device 100A according to the second embodiment are performed as described above.

<4. Third Embodiment>

(Third Structure)

Figure 8:
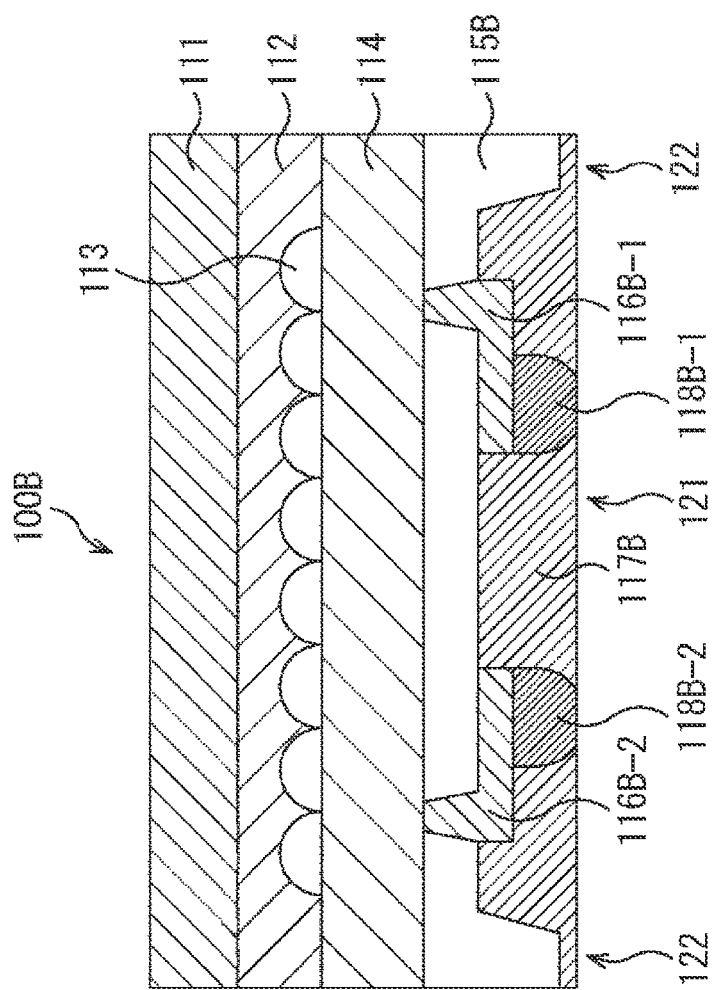
FIG. 8 is a cross-sectional view illustrating an example of a structure of an imaging device according to a third embodiment.

FIG. 8 is a cross-sectional view illustrating an example of a structure of an imaging device according to a third embodiment.

In the imaging device 100B of FIG. 8, portions that are the same as or correspond to those of the imaging device 100A of FIG. 5 will be denoted by the same or corresponding reference numerals. The imaging device 100B of FIG. 8 is different in a part of a structure of a second substrate 115B from the imaging device 100A of FIG. 5.

Specifically, in the imaging device 100B of FIG. 8, a dug portion 121 having sidewalls of a forward tapered shape is formed in silicon (Si) of the second substrate 115B, and parts of TSV/RDL wirings 116B-1 and 116B-2 and solder balls 118B-1 and 118B-2 are formed in the dug portion 121. Furthermore, a solder mask 117B is formed in the dug portion 121 so as to cover the TSV/RDL wirings 116B-1 and 116B-2 and the solder balls 118B-1 and 118B-2.

Here, in the imaging device 100B of FIG. 8, the solder mask 117B is also applied to a region of a frame shape (regions of a frame portion 122 and a scribe portion 131), and the solder balls 118B-1 and 118B-2 are planarized so as to be flush with a surface of the solder mask 117B applied to the region of the frame shape. In other words, in a terminal extraction surface, the surface of the solder mask 117B and surfaces of the solder balls 118B-1 and 118B-2 are flush with each other.

As described above, the imaging device 100B of FIG. 8 is different in structures of the solder balls 118B-1 and 118B-2 and the solder mask 117B from the imaging device 100A of FIG. 5, but is the same as the imaging device 100A of FIG. 5 in that, in the second substrate 115B, silicon (Si) is dug to form the dug portion 121 having the sidewalls of the forward tapered shape and thus form a structure in which a film thickness of silicon (Si) in the region of the frame shape (the regions of the frame portion 122 and the scribe portion 131) is not reduced.

With this arrangement, silicon (Si) has a sufficient film thickness in the region of the frame shape (the regions of the frame portion 122 and the scribe portion 131), and sufficient chip hardness can thus be secured in a semiconductor chip including the first substrate 114 (image sensor) and the second substrate 115B (logic circuit). Furthermore, since parts of the TSV/RDL wirings 116B-1 and 116B-2 or the solder balls 118B-1 and 118B-2 are formed in the dug portion 121 formed in silicon (Si) of the second substrate 115B, a height of the imaging device 100B as a semiconductor package can be reduced as compared with a structure of the general imaging device 1 (FIG. 1).

As described above, in a case where the imaging device 100B according to the third embodiment has a backside RDL electrode structure, the imaging device 100B has a structure in which the dug portion 121 is formed in silicon (Si) of the second substrate 115B, parts of the TSV/RDL wirings 116B-1 and 116B-2 and the solder balls 118B-1 and 118B-2 are formed in the dug portion 121, and the solder mask 117B is embedded in the dug portion 121. Since the imaging device 100B according to the third embodiment has such a structure, it is possible to reduce a height of the semiconductor package and secure a chip strength of the semiconductor chip.

Furthermore, in the imaging device 100B according to the third embodiment, the surface of the solder mask 117B and the surfaces of the solder balls 118B-1 and 118B-2 are flush with each other, a surface (silicon (Si) surface) of the frame portion 122 is covered by the solder mask 117B, and the silicon (Si) surface of the second substrate 115B can thus be protected without being exposed.

Note that processes of manufacturing the imaging device 100B according to the third embodiment are substantially similar to the processes (FIGS. 6A, 6B, 6C, 7A, 7B, and 7C) of manufacturing the imaging device 100A according to the second embodiment, and a detailed description thereof is thus omitted, but in the planarization process (FIG. 7C), the surface of the solder mask 117B and the surfaces of the solder balls 118B-1 and 118B-2 are planarized so as to be flush with each other.

<5. Fourth Embodiment>
(Fourth Structure)
FIG. 9 is a cross-sectional view illustrating an example of a structure of an imaging device according to a fourth embodiment.

Figure 9:
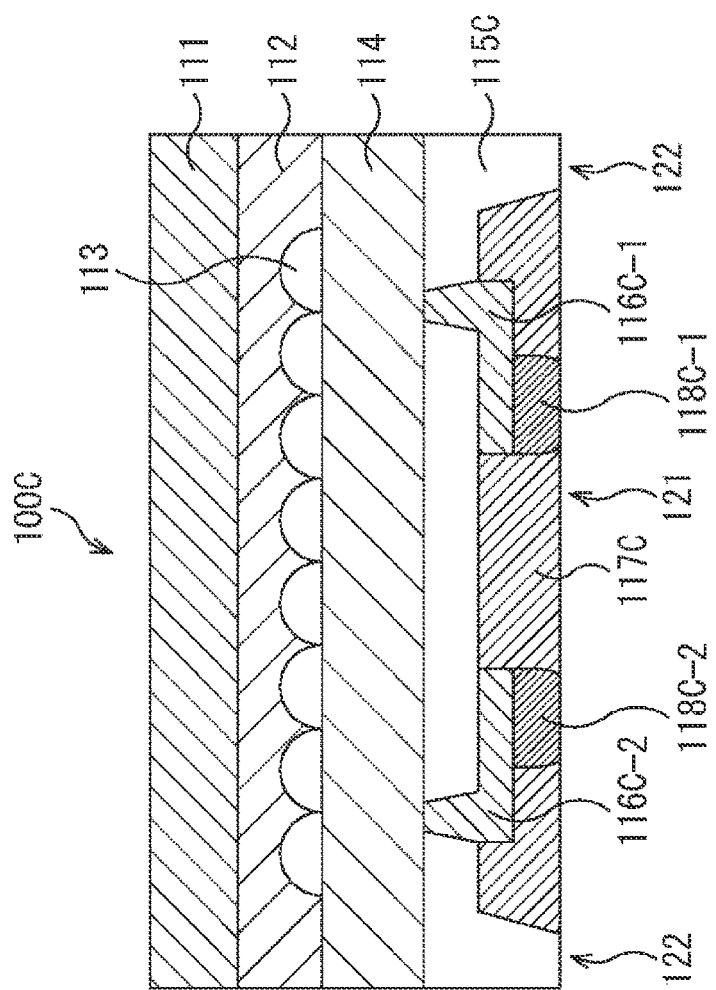
FIG. 9 is a cross-sectional view illustrating an example of a structure of an imaging device according to a fourth embodiment.

In the imaging device 100C of FIG. 9, portions that are the same as or correspond to those of the imaging device 100A of FIG. 5 will be denoted by the same or corresponding reference numerals. The imaging device 100C of FIG. 9 is different in a part of a structure of a second substrate 115C from the imaging device 100A of FIG. 5.

Specifically, in the imaging device 100C of FIG. 9, a dug portion 121 having sidewalls of a forward tapered shape is formed in silicon (Si) of the second substrate 115C, and TSV/RDL wirings 116C-1 and 116C-2 and solder balls 118C-1 and 118C-2 are formed in the dug portion 121. Furthermore, a solder mask 117C is formed in the dug portion 121 so as to cover the TSV/RDL wirings 116C-1 and 116C-2 and the solder balls 118C-1 and 118C-2.

Here, in (a terminal extraction surface of) the imaging device 100C of FIG. 9, a surface (silicon (Si) surface) of a region of a frame shape (regions of a frame portion 122 and a scribe portion 131), a surface of the solder mask 117C, and surfaces of the solder balls 118C-1 and 118C-2 are planarized to be flush with one another.

As described above, the imaging device 100C of FIG. 9 is different in structures of the solder balls 118C-1 and 118C-2 and the solder mask 117C from the imaging device 100A of FIG. 5, but is the same as the imaging device 100A of FIG. 5 in that, in the second substrate 115C, silicon (Si) is dug to form the dug portion 121 having the sidewalls of the forward tapered shape and thus form a structure in which a film thickness of silicon (Si) in the region of the frame shape (the regions of the frame portion 122 and the scribe portion 131) is not reduced.

With this arrangement, silicon (Si) has a sufficient film thickness in the region of the frame shape (the regions of the frame portion 122 and the scribe portion 131), and sufficient chip hardness can thus be secured in a semiconductor chip including the first substrate 114 (image sensor) and the second substrate 115C (logic circuit). Furthermore, since the TSV/RDL wirings 116C-1 and 116C-2 or the solder balls 118C-1 and 118C-2 are formed in the dug portion 121 formed in silicon (Si) of the second substrate 115C, a height of the imaging device 100C as a semiconductor package can be reduced as compared with a structure of the general imaging device 1 (FIG. 1).

As described above, in a case where the imaging device 100C according to the fourth embodiment has a backside RDL electrode structure, the imaging device 100C has a structure in which the dug portion 121 is formed in silicon (Si) of the second substrate 115C, the TSV/RDL wirings 116C-1 and 116C-2 and the solder balls 118C-1 and 118C-2 are formed in the dug portion 121, and the solder mask 117C is embedded in the dug portion 121. Since the imaging device 100C according to the fourth embodiment has such a structure, it is possible to reduce a height of the semiconductor package and secure a chip strength of the semiconductor chip.

Furthermore, in the imaging device 100C according to the fourth embodiment, the surface of the solder mask 117C and the surfaces of the solder balls 118C-1 and 118C-2 are flush with the surface (silicon (Si) surface) of the region of the frame shape, and it is possible to make a thickness of the imaging device 100C as a semiconductor package the smallest as compared with the other embodiments. Furthermore, since a lower surface (terminal extraction surface) of the second substrate 115C becomes flat, the imaging device 100C is easily handled. For example, when the imaging device 100C is stuck to an organic substrate, the imaging device 100C is easily stuck to the organic substrate.

Note that processes of manufacturing the imaging device 100C according to the fourth embodiment are substantially similar to the processes (FIGS. 6A, 6B, 6C, 7A, 7B, and 7C) of manufacturing the imaging device 100A according to the second embodiment, and a detailed description thereof is thus omitted, but in the planarization process (FIG. 7C), the surface (silicon (Si) surface) of the frame portion 122, the surface of the solder mask 117C, and the surfaces of the solder balls 118C-1 and 118C-2 are planarized so as to be flush with one another.

Figure 10:
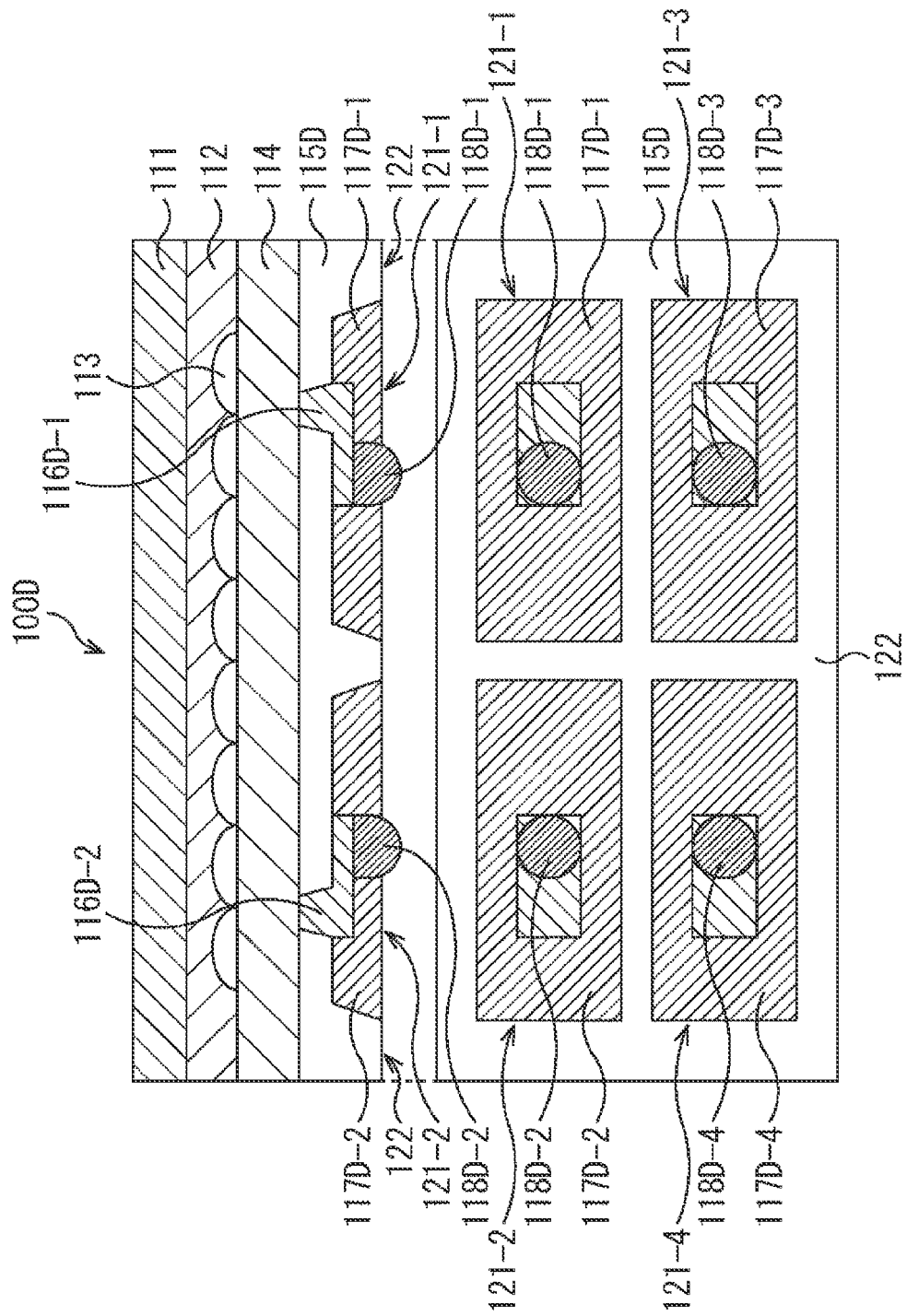
FIG. 10 is a view (a cross-sectional view and a bottom view) illustrating an example of a structure of an imaging device according to a fifth embodiment.

<6. Fifth Embodiment>
(Fifth Structure)
FIG. 10 is a view illustrating an example of a structure of an imaging device according to a fifth embodiment. A cross-sectional view of the imaging device 100D is illustrated on an upper side of FIG. 10, and a bottom view of the imaging device 100D is illustrated on a lower side of FIG. 10.

The imaging device 100D of FIG. 10 is a semiconductor package on which a large semiconductor chip (large image sensor) is mounted as compared to a general semiconductor chip. Note that in the imaging device 100D of FIG. 10, portions that are the same as or correspond to those of the imaging device 100 of FIG. 2 or the imaging device 100A of FIG. 5 will be denoted by the same or corresponding reference numerals. The imaging device 100D of FIG. 10 is different in a part of a structure of a second substrate 115D from the imaging device 100 or the like of FIG. 2.

Specifically, in the imaging device 100D of FIG. 10, silicon (Si) of the second substrate 115D is dug, such that a dug portion 121 is formed, similarly to the imaging device 100 of FIG. 2 or the like, but the imaging device 100D of FIG. 10 is different from the imaging device 100 of FIG. 2 in that a region in which silicon (Si) is not dug is provided in a central portion of a semiconductor chip.

In other words, in the imaging device 100D of FIG. 10, four dug portions 121-1 to 121-4 are separately formed in silicon (Si) of the second substrate 115D depending on regions in which TSV/RDL wirings 116D and solder balls 118D are formed, such that a region in which silicon (Si) is not dug is formed at a central portion of a large semiconductor chip.

More specifically, a TSV/RDL wiring 116D-1 and a solder ball 118D-1 are formed in a dug portion 121-1 of dug portions 121-1 to 121-4 formed in silicon (Si) of the second substrate 115D and having sidewalls of a forward tapered shape, and a solder mask 117D-1 is formed so as to cover the TSV/RDL wiring 116D-1 and the solder ball 118D-1.

Similarly, a TSV/RDL wiring 116D-2 and a solder ball 118D-2 are formed in the dug portion 121-2 and a solder mask 117D-2 is formed so as to cover the TSV/RDL wiring 116D-2 and the solder ball 118D-2. Moreover, a TSV/RDL wiring 116D-3 and a solder ball 118D-3 are formed in the dug portion 121-3 and a solder mask 117D-3 is formed so as to cover the TSV/RDL wiring 116D-3 and the solder ball 118D-3, and a TSV/RDL wiring 116D-4 and a solder ball 118D-4 are formed in the dug portion 121-4 and a solder mask 117D-4 is formed so as to cover the TSV/RDL wiring 116D-4 and the solder ball 118D-4.

As described above, when the semiconductor chip becomes large, there is a possibility that a deflection will become large at a peripheral portion or the like of the semiconductor chip, but in the imaging device 100D of FIG. 10, the region in which the silicon (Si) of the second substrate 115D is not dug is formed at a central portion of the large semiconductor chip to provide tension to the central portion, such that warpage or the like of the semiconductor chip is suppressed.

Note that the region in which silicon (Si) of the second substrate 115D is not dug has a cross square shape in FIG. 10, but a shape of the region in which the silicon (Si) is not dug is arbitrary. For example, in order to further increase a strength of the semiconductor chip to suppress the warpage of the semiconductor chip, it is sufficient to increase the region in which silicon (Si) is not dug in a longitudinal direction and a transverse direction, but the number of terminals that can be extracted from a terminal extraction surface is reduced by the increased region, and the region in which silicon (Si) is not dug can thus be determined depending on the number of terminals that are required.

Furthermore, similarly to the imaging device 100 of FIG. 2, or the like, in the imaging device 100D of FIG. 10, in the second substrate 115D, silicon (Si) is dug to form the dug portions 121-1 to 121-4 having the sidewalls of the forward tapered shape and thus form a structure in which a film thickness of silicon (Si) in the region of the cross square shape is not reduced.

With this arrangement, silicon (Si) has a sufficient film thickness in the region of the cross square shape, and sufficient chip hardness can thus be secured in a semiconductor chip (large semiconductor chip) including the first substrate 114 (large image sensor) and the second substrate 115D (logic circuit). Furthermore, since the TSV/RDL wirings 116D-1 to 116D-4 or the solder balls 118D-1 to 118D-4 are formed in the dug portion 121 formed in silicon (Si) of the second substrate 115D, a height of the imaging device 100D as a semiconductor package can be reduced as compared with a structure of the general imaging device 1 (FIG. 1).

As described above, in a case where the imaging device 100D according to the fifth embodiment has a backside RDL electrode structure, the imaging device 100D has a structure in which the dug portions 121-1 to 121-4 are formed in silicon (Si) of the second substrate 115D, the TSV/RDL wirings 116D-1 to 116D-4 and the solder balls 118D-1 to 118D-4 are formed in the dug portions 121-1 to 121-4, respectively, and the solder masks 117D-1 to 117D-4 are embedded in the dug portions 121-1 to 121-4, respectively. Since the imaging device 100D according to the fifth embodiment has such a structure, it is possible to reduce a height of the semiconductor package and secure a chip strength of the semiconductor chip.

Note that processes of manufacturing the imaging device 100D according to the fifth embodiment are substantially similar to the processes (FIGS. 3A, 3B, 3C, 4A, 4B, and 4C) of manufacturing the imaging device 100 according to the first embodiment or the processes (FIGS. 6A, 6B, 6C, 7A, 7B, and 7C) of manufacturing the imaging device 100A according to the second embodiment, and a detailed description thereof is thus omitted, but similar manufacturing processes are performed on each of the dug portions 121-1 to 121-4 formed in silicon (Si) of the second substrate 115D.

<7. Sixth Embodiment>
(Sixth Structure)
FIG. 11 is a cross-sectional view illustrating an example of a structure of an imaging device according to a sixth embodiment.

Figure 11:
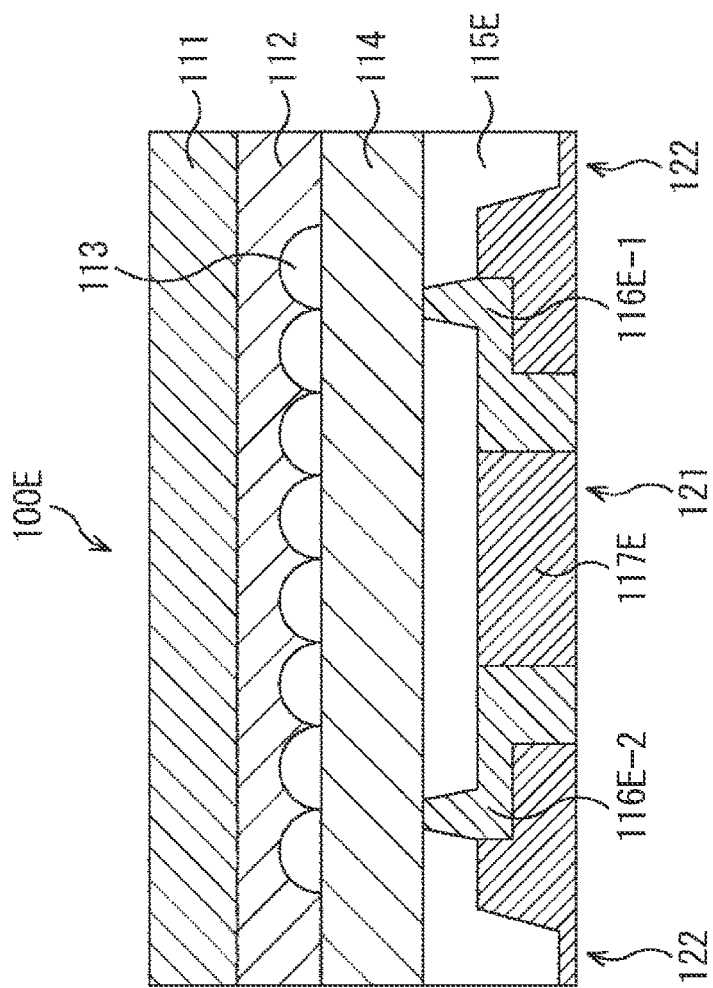
FIG. 11 is a cross-sectional view illustrating an example of a structure of an imaging device according to a sixth embodiment.

In the imaging device 100E of FIG. 11, portions that are the same as or correspond to those of the imaging device 100A of FIG. 5 will be denoted by the same or corresponding reference numerals. The imaging device 100E of FIG. 11 is different in a part of a structure of a second substrate 115E from the imaging device 100A of FIG. 5.

Specifically, in the imaging device 100E of FIG. 11, a dug portion 121 having sidewalls of a forward tapered shape is formed in silicon (Si) of the second substrate 115E, and TSV/RDL wirings 116E-1 and 116E-2 are formed in the dug portion 121.

However, here, instead of the solder balls 118A-1 and 118A-2 illustrated in FIG. 5, Cu-land grid arrays (LGAs) are formed for the TSV/RDL wirings 116E-1 and 116E-2, and are used as electrodes for connection. Furthermore, a solder mask 117E is formed in the dug portion 121 so as to cover the TSV/RDL wirings 116E-1 and 116E-2, but surfaces of the TSV/RDL wirings 116E-1 and 116E-2 (surfaces of the electrodes for connection) are planarized so as to be flush with a surface of the solder mask 117E.

As described above, the imaging device 100E of FIG. 11 is different from the imaging device 100A of FIG. 5 in that the Cu-LGAs are formed for the TSV/RDL wirings 116E-1 and 116E-2 and are used as the electrodes for connection, but is the same as the imaging device 100A of FIG. 5 in that, in the second substrate 115E, silicon (Si) is dug to form the dug portion 121 having the sidewalls of the forward tapered shape and thus form a structure in which a film thickness of silicon (Si) in a region of a frame shape (regions of a frame portion 122 and a scribe portion 131) is not reduced.

With this arrangement, silicon (Si) has a sufficient film thickness in the region of the frame shape (the regions of the frame portion 122 and the scribe portion 131), and sufficient chip hardness can thus be secured in a semiconductor chip including the first substrate 114 (image sensor) and the second substrate 115E (logic circuit). Furthermore, since the TSV/RDL wirings 116E-1 and 116E-2 are formed in the dug portion 121 formed in silicon (Si) of the second substrate 115E, a height of the imaging device 100E as a semiconductor package can be reduced as compared with a structure of the general imaging device 1 (FIG. 1).

As described above, in a case where the imaging device 100E according to the sixth embodiment has a backside RDL electrode structure, the imaging device 100E has a structure in which the dug portion 121 is formed in silicon (Si) of the second substrate 115E, the TSV/RDL wirings 116E-1 and 116E-2 are formed in the dug portion 121, and the solder mask 117E is embedded in the dug portion 121. Since the imaging device 100E according to the sixth embodiment has such a structure, it is possible to reduce a height of the semiconductor package and secure a chip strength of the semiconductor chip.

Furthermore, in the imaging device 100E of the sixth embodiment, it is not necessary to provide solder balls 118 by forming the Cu-LGAs as the electrodes for connection for the TSV/RDL wirings 116E-1 and 116E-2, and it is thus possible to reduce a thickness of the imaging device 100E as the semiconductor package as compared with the other embodiments in which the solder balls 118 are provided.

Note that processes of manufacturing the imaging device 100E according to the sixth embodiment correspond to the processes (FIGS. 6A, 6B, 6C, 7A, 7B, and 7C) of manufacturing the imaging device 100A according to the second embodiment, and a detailed description thereof is thus omitted, but the processes of manufacturing the imaging device 100E are different from the processes (FIGS. 6A, 6B, 6C, 7A, 7B, and 7C) of manufacturing the imaging device 100A according to the second embodiment in that a patterning process for defining positions at which the solder balls 118A-1 and 118A-2 are to be mounted or the solder ball mounting and reflow process is not required as well as the TSV/RDL wirings 116E-1 and 116E-2 or the Cu-LGAs, which are electrodes for connection, are formed in the dug portion 121 in the TSV/RDL forming process (FIG. 6C).

<8. Seventh Embodiment>
(Seventh Structure)
FIG. 12 is a cross-sectional view illustrating an example of a structure of an imaging device according to a seventh embodiment.

Figure 12:
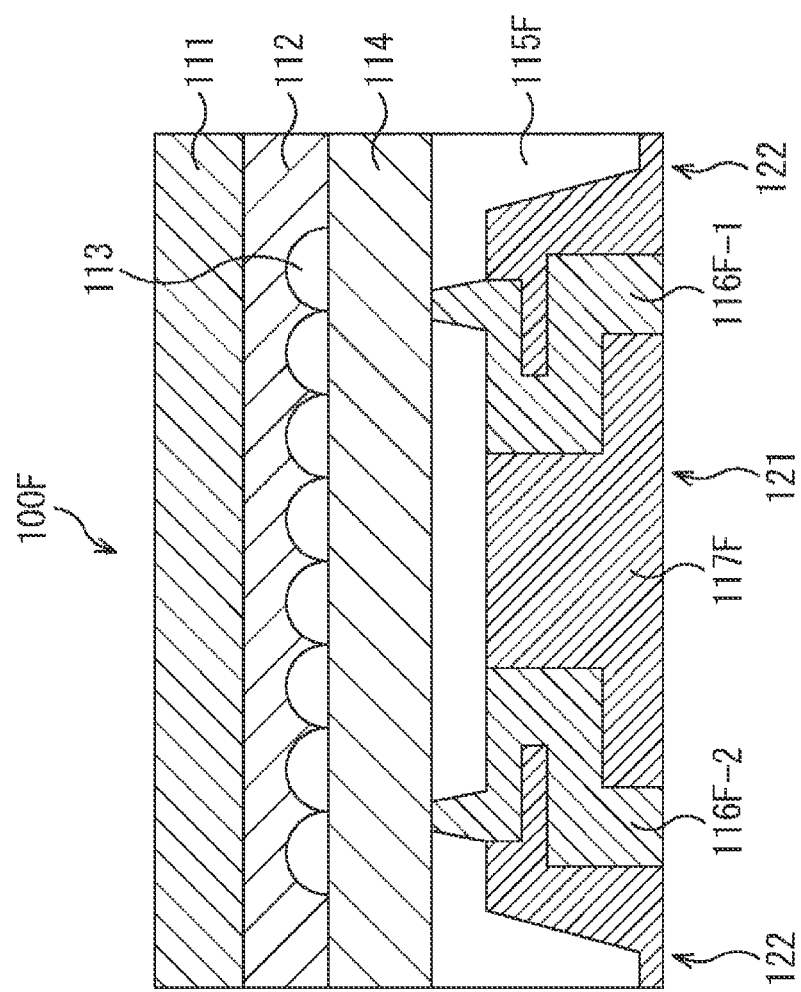
FIG. 12 is a cross-sectional view illustrating an example of a structure of an imaging device according to a seventh embodiment.

In the imaging device 100F of FIG. 12, portions that are the same as or correspond to those of the imaging device 100A of FIG. 5 will be denoted by the same or corresponding reference numerals. The imaging device 100F of FIG. 12 is different in a part of a structure of a second substrate 115F from the imaging device 100A of FIG. 5.

Specifically, similarly to the imaging device 100E of FIG. 11, in the imaging device 100F of FIG. 12, a dug portion 121 having sidewalls of a forward tapered shape is formed in silicon (Si) of the second substrate 115F, and multilayer wirings 116F-1 and 116F-2 are formed in the dug portion 121.

Here, multilayer RDL wirings 116F-1 and 116F-2 include a plurality of redistribution layers (RDLs). For example, the multilayer RDL wirings 116F-1 and 116F-2 include an uppermost wiring layer closest to the first substrate 114, a middle wiring layer, and a lowermost wiring layer farthest from the first substrate 114.

As described above, the imaging device 100F of FIG. 12 is different from the imaging device 100A of FIG. 5 in that the multilayer RDL wirings 116F-1 and 116F-2 are formed in the dug portion 121, but is the same as the imaging device 100A of FIG. 5 in that, in the second substrate 115F, silicon (Si) is dug to form the dug portion 121 having the sidewalls of the forward tapered shape and thus form a structure in which a film thickness of silicon (Si) in a region of a frame shape (regions of a frame portion 122 and a scribe portion 131) is not reduced.

With this arrangement, silicon (Si) has a sufficient film thickness in the region of the frame shape (the regions of the frame portion 122 and the scribe portion 131), and sufficient chip hardness can thus be secured in a semiconductor chip including the first substrate 114 (image sensor) and the second substrate 115F (logic circuit). Furthermore, since the multilayer RDL wirings 116F-1 and 116F-2 are formed in the dug portion 121 formed in silicon (Si) of the second substrate 115F, a height of the imaging device 100F as a semiconductor package can be reduced as compared with a structure of the general imaging device 1 (FIG. 1).

As described above, in a case where the imaging device 100F according to the seventh embodiment has a backside RDL electrode structure, the imaging device 100F has a structure in which the dug portion 121 is formed in silicon (Si) of the second substrate 115F, the multilayer RDL wirings 116F-1 and 116F-2 are formed in the dug portion 121, and the solder mask 117F is embedded in the dug portion 121. Since the imaging device 100F according to the seventh embodiment has such a structure, it is possible to reduce a height of the semiconductor package and secure a chip strength of the semiconductor chip.

Note that processes of manufacturing the imaging device 100F according to the seventh embodiment correspond to the processes (FIGS. 6A, 6B, 6C, 7A, 7B, and 7C) of manufacturing the imaging device 100A according to the second embodiment, and a detailed description thereof is thus omitted, but the processes of manufacturing the imaging device 100F are different from the processes (FIGS. 6A, 6B, 6C, 7A, 7B, and 7C) of manufacturing the imaging device 100A according to the second embodiment in that a patterning process for defining positions at which the solder balls 118A-1 and 118A-2 are to be mounted or the solder ball mounting and reflow process is not required as well as the multilayer RDL wirings 116F-1 and 116F-2 are formed in the dug portion 121 in the TSV/RDL forming process (FIG. 6C).

<9. Eighth Embodiment>
(Eighth Structure)
FIG. 13 is a cross-sectional view illustrating an example of a structure of an imaging device according to an eighth embodiment.

Figure 13:
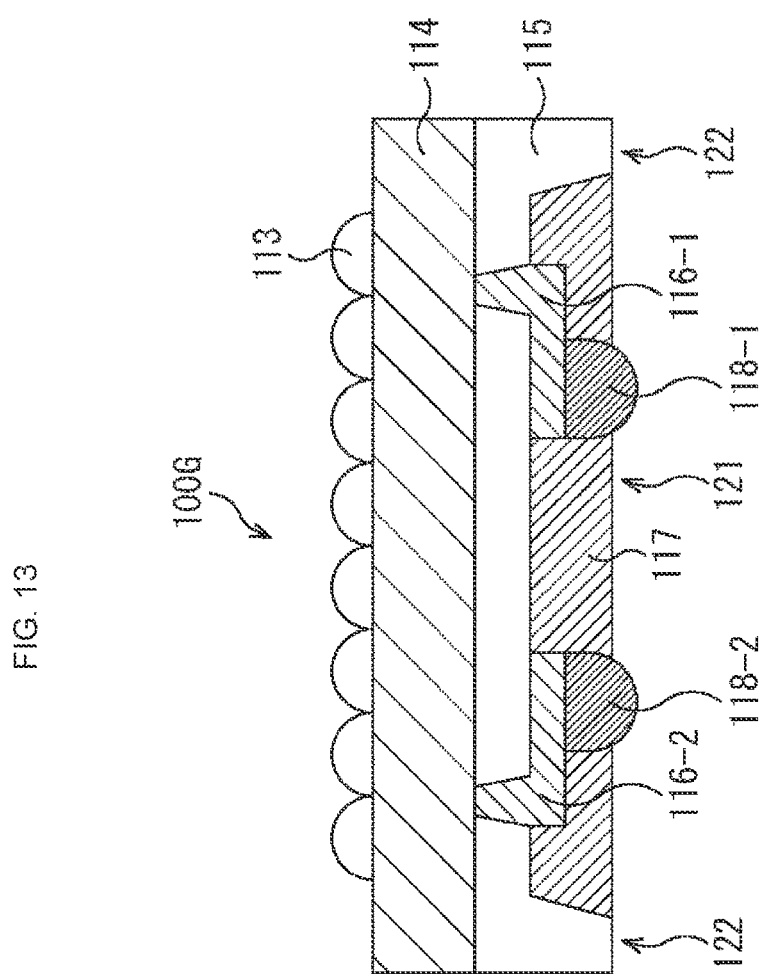
FIG. 13 is a cross-sectional view illustrating an example of a structure of an imaging device according to an eighth embodiment.

In the imaging device 100G of FIG. 13, portions that are the same as or correspond to those of the imaging device 100 of FIG. 2 will be denoted by the same or corresponding reference numerals. The imaging device 100G of FIG. 13 is different from the imaging device 100 of FIG. 2 in that a transparent member 111 such as glass or the like is not fixed to a first substrate 114 on which on-chip lenses 113 are formed, by an adhesive 112.

As described above, the imaging device 100G of FIG. 13 is the same as the imaging device 100 of FIG. 2 in that even in a case where the transparent member 111 is not stacked on the first substrate 114, in a second substrate 115, silicon (Si) is dug to form a dug portion 121 having sidewalls of a forward tapered shape and thus form a structure in which a film thickness of silicon (Si) in a region of a frame shape (regions of a frame portion 122 and a scribe portion 131) is not reduced.

With this arrangement, silicon (Si) has a sufficient film thickness in the region of the frame shape (the regions of the frame portion 122 and the scribe portion 131), and sufficient chip hardness can thus be secured in a semiconductor chip including the first substrate 114 (image sensor) and the second substrate 115 (logic circuit). Furthermore, since parts of TSV/RDL wirings 116-1 and 116-2 or solder balls 118-1 and 118-2 are formed in the dug portion 121 formed in silicon (Si) of the second substrate 115, a height of the imaging device 100G as a semiconductor package can be reduced as compared with a structure of the general imaging device 1 (FIG. 1).

As described above, in a case where the imaging device 100G according to the eighth embodiment has a backside RDL electrode structure, the imaging device 100G has a structure in which the dug portion 121 is formed in silicon (Si) of the second substrate 115, parts of the TSV/RDL wirings 116-1 and 116-2 and the solder balls 118-1 and 118-2 are formed in the dug portion 121, and a solder mask 117 is embedded in the dug portion 121. Since the imaging device 100G according to the eighth embodiment has such a structure, it is possible to reduce a height of the semiconductor package and secure a chip strength of the semiconductor chip.

Note that a structure corresponding to the first embodiment has been described by way of example in the eighth embodiment, but a structure in which the transparent member 111 is not stacked on the first substrate 114 can also be similarly adopted in the second to seventh embodiments.

<10. Configuration of Electronic Apparatus>

Figure 14:
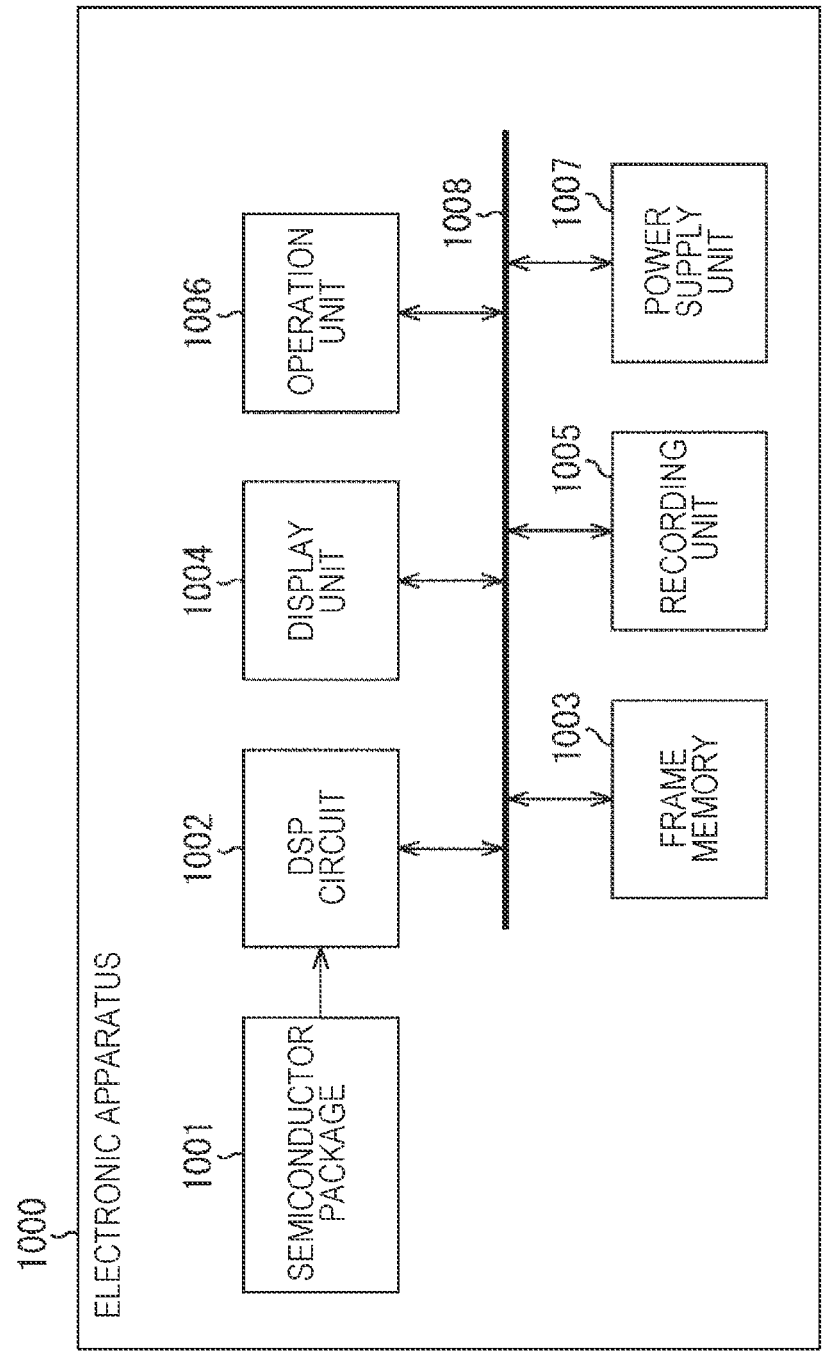
FIG. 14 is a block diagram illustrating a configuration example of an electronic apparatus having an imaging device to which the present technology is applied.

FIG. 14 is a block diagram illustrating a configuration example of an electronic apparatus 1000 having an imaging device to which the present technology is applied.

The electronic apparatus 1000 is, for example, an electronic apparatus such as an imaging device such as a digital still camera, a video camera or the like, or a portable terminal device such as a smartphone, a tablet type terminal or the like.

The electronic apparatus 1000 includes a semiconductor package 1001, a digital signal processing (DSP) circuit 1002, a frame memory 1003, a display unit 1004, a recording unit 1005, an operation unit 1006, and a power supply unit 1007. Furthermore, in the electronic apparatus 1000, the DSP circuit 1002, the frame memory 1003, the display unit 1004, the recording unit 1005, the operation unit 1006, and the power supply unit 1007 are connected to each other through a bus line 1008.

The semiconductor package 1001 corresponds to the imaging device 100 or the like according to the first embodiment described above, and has the structure illustrated in FIG. 2 or the like.

In other words, in the semiconductor package 1001, in a case where the first substrate 114 (image sensor) and the second substrate 115 (logic circuit) are stacked, when the semiconductor package 1001 has a backside RDL electrode structure in which terminals are extracted from a lower surface side of the first substrate 114, the dug portion 121 is formed in silicon (Si) of the second substrate 115. The TSV/RDL wirings 116-1 and 116-2 and the solder balls 118-1 and 118-2 are formed in the dug portion 121, and the solder mask 117 is embedded in the dug portion 121.

The DSP circuit 1002 is a camera signal processing circuit that processes a signal supplied from the semiconductor package 1001. The DSP circuit 1002 outputs image data obtained by processing the signal supplied from the semiconductor package 1001. The frame memory 1003 temporarily holds the image data processed by the DSP circuit 1002 in frame units.

The display unit 1004 includes, for example, a panel-type display device such as a liquid crystal panel, an organic electroluminescence (EL) panel or the like, and displays a moving image or a still image captured by the semiconductor package 1001. The recording unit 1005 records image data of the moving image or the still image captured by the semiconductor package 1001 in a recording medium such as a semiconductor memory, a hard disk or the like.

The operation unit 1006 outputs operation commands for various functions of the electronic apparatus 1000 according to an operation by a user. The power supply unit 1007 appropriately supplies various types of power that becomes operation power of the DSP circuit 1002, the frame memory 1003, the display unit 1004, the recording unit 1005, and the operation unit 1006 to these supply targets.

The electronic apparatus 1000 is configured as described above. A technology according to the present disclosure is applied to the semiconductor package 1001 as described above.

Specifically, by applying the technology according to the present disclosure to the semiconductor package 1001, silicon (Si) has a sufficient film thickness in the region of the frame shape (the regions of the frame portion 122 and the scribe portion 131), and sufficient chip hardness can thus be secured in a semiconductor chip including the first substrate 114 (image sensor) and the second substrate 115 (logic circuit).

Furthermore, in the semiconductor package 1001, (parts of) the TSV/RDL wirings 116-1 and 116-2 or the solder balls 118-1 and 118-2 are formed in the dug portion 121 formed in silicon (Si) of the second substrate 115, and a height of the semiconductor package 1001 can thus be reduced as compared with a structure of the general imaging device 1 (FIG. 1).

<11. Use Example of Imaging Device>

Figure 15:
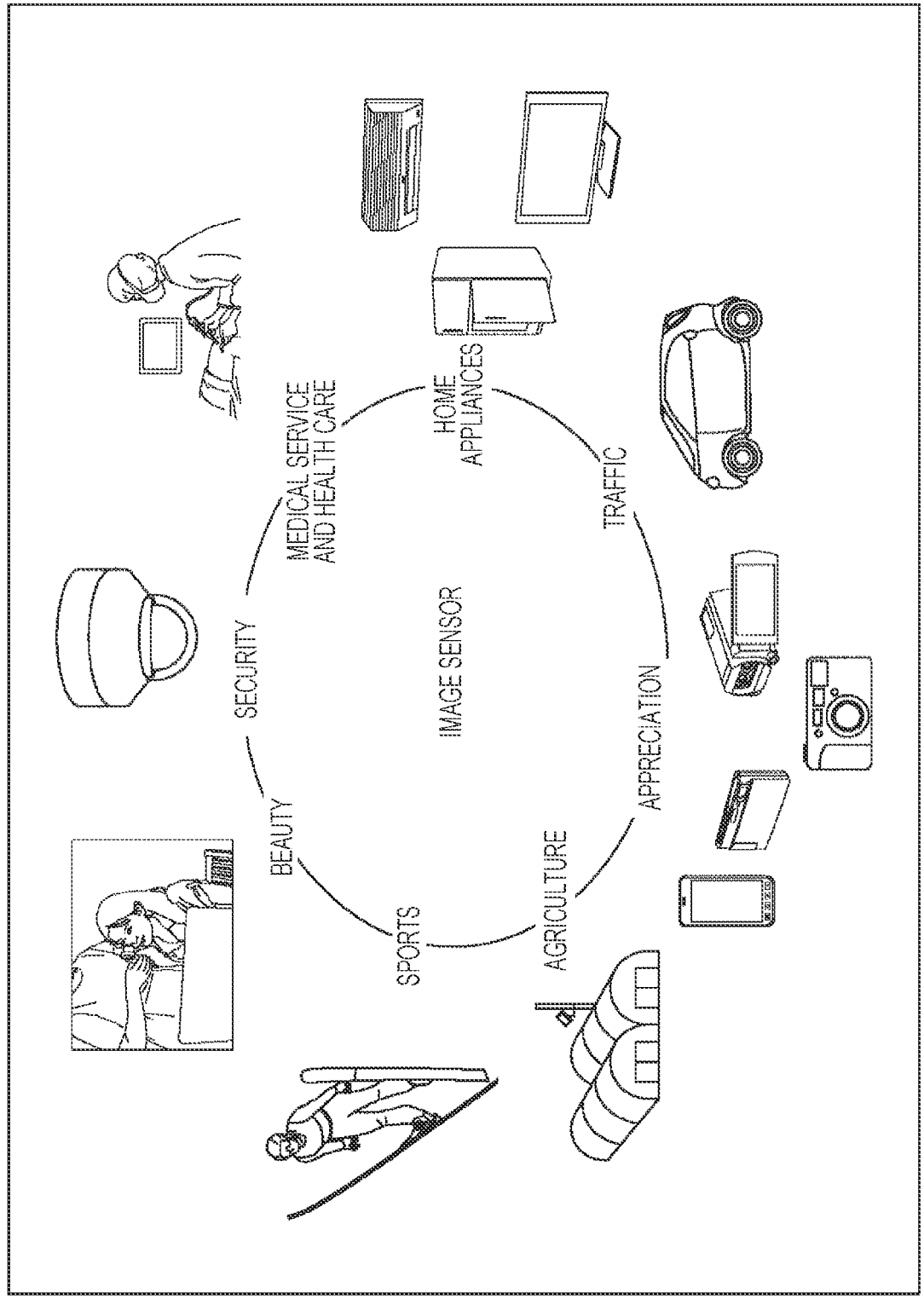
FIG. 15 is a view illustrating a use example of an imaging device to which the present technology is applied.

FIG. 15 is a view illustrating a use example of an imaging device to which the present technology is applied.

The imaging device 100 (semiconductor package) having the first substrate 114 as an image sensor can be used in various cases of sensing light such as visible light, infrared light, ultraviolet light, X-rays, or the like, as follows. In other words, as illustrated in FIG. 15, the imaging device 100 or the like can also be used in devices used in, for example, a traffic field, a home appliances field, a medical and healthcare field, a security field, a beauty field, a sports field, an agriculture field, and the like, as well as an appreciation field that an image provided for appreciation is captured.

Specifically, as described above, in the appreciation field, the imaging device 100 or the like can be used in, for example, a device (for example, the electronic apparatus 1000 of FIG. 14) for capturing an image provided for appreciation, such as a digital camera, a smartphone, a mobile phone with a camera function, or the like.

In the traffic field, the imaging device 100 or the like can be used in, for example, a device provided for traffic, such as an in-vehicle sensor that captures the front or the rear, the surroundings, the inside, and the like, of a vehicle, a monitoring camera that monitors a traveling vehicle and a road, a distance measurement sensor that measures a distance between vehicles, or the like, for safe driving such as automatic stop or the like, recognition of a driver state or the like.

In the home appliances field, the imaging device 100 or the like can be used in, for example, a device provided for home appliances such as a television receiver, a refrigerator, an air conditioner, and the like, in order to capture a user's gesture and perform an apparatus operation depending on the gesture. Furthermore, in the medical and healthcare field, the imaging device 100 or the like can be used in, for example, a device provided for medical service and healthcare, such as an endoscope, a device that performs blood vessel image capture by receiving infrared light, or the like.

In the security field, the imaging device 100 or the like can be used in, for example, a device provided for security, such as a monitoring camera for crime prevention, a camera for person authentication, or the like. Furthermore, in the beauty field, the imaging device 100 or the like can be used in, for example, a device provided for beauty, such as a skin measuring instrument that captures the skin, a microscope that captures the scalp, or the like.

In the sports field, the imaging device 100 or the like can be used in, for example, a device provided for sports, such as an action camera, a wearable camera for sports, or the like. Furthermore, in the agriculture field, the imaging device 100 or the like can be used in, for example, a device provided for agriculture, such as a camera monitoring a condition of fields or crops.

<12. Application Example to In-Vivo Information Acquisition System>

The technology according to the present disclosure (the present technology) can be applied to various products. For example, the technology according to the present disclosure may be applied to an endoscopic surgery system.

Figure 16:
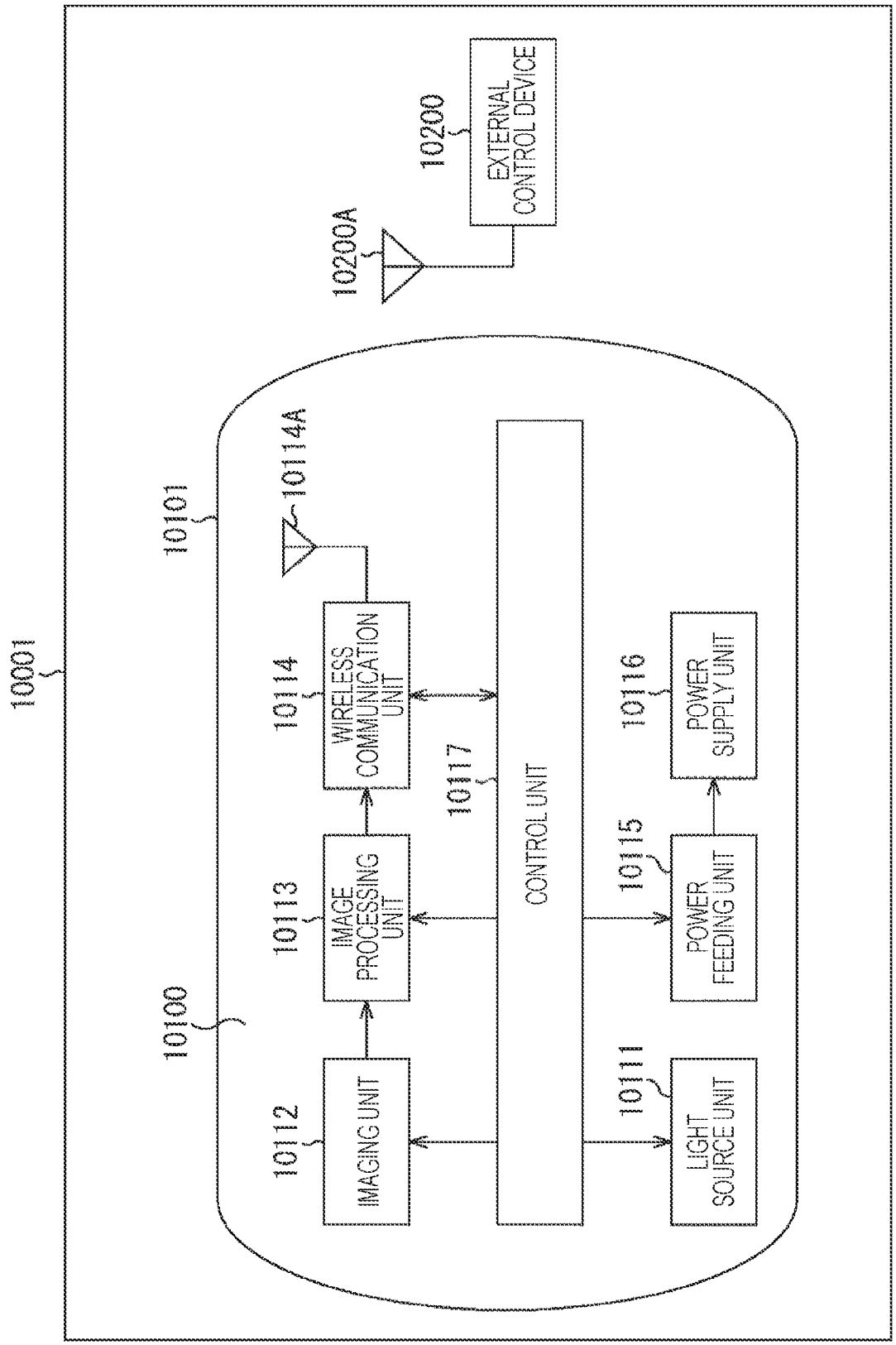
FIG. 16 is a block diagram illustrating an example of a schematic configuration of an in-vivo information acquisition system.

FIG. 16 is a block diagram illustrating an example of a schematic configuration of an in-vivo information acquisition system of a patient using a capsule type endoscope to which the technology according to the present disclosure (the present technology) can be applied.

The in-vivo information acquisition system 10001 includes a capsule type endoscope 10100 and an external control device 10200.

The capsule type endoscope 10100 is swallowed by the patient at the time of examination. The capsule type endoscope 10100 has an imaging function and a wireless communication function, and sequentially captures images of the inside of the organ (hereinafter, also referred to as in-vivo images) at predetermined intervals and sequentially wirelessly transmits information regarding the in-vivo images to the external control device 10200 outside the body, while moving inside the organ such as the stomach or intestine by peristaltic movement or the like during a period until it is naturally discharged from the patient.

The external control device 10200 generally controls an operation of the in-vivo information acquisition system 10001. Furthermore, the external control device 10200 receives the information regarding the in-vivo images transmitted from the capsule type endoscope 10100, and generates image data for displaying the in-vivo images on a display device (not illustrated) on the basis of the received information regarding the in-vivo images.

In this way, the in-vivo information acquisition system 10001 can obtain the in-vivo images at any time by capturing an image of a state in the patient's body during a period from at a time when the capsule type endoscope 10100 is swallowed until the capsule type endoscope 10100 is discharged.

Configurations and functions of the capsule type endoscope 10100 and the external control device 10200 will be described in more detail.

The capsule type endoscope 10100 has a capsule type housing 10101, and a light source unit 10111, an imaging unit 10112, an image processing unit 10113, a wireless communication unit 10114, a power feeding unit 10115, a power supply unit 10116, and a control unit 10117 are housed in the housing 10101.

The light source unit 10111 includes, for example, a light source such as a light emitting diode (LED), and irradiates light to an imaging visual field of the imaging unit 10112.

The imaging unit 10112 includes an imaging element and an optical system including a plurality of lenses provided in front of the imaging element. Reflected light (hereinafter, referred to as observation light) of light irradiated to a body tissue, which is an observation target, is collected by the optical system and is incident on the imaging element. In the imaging unit 10112, in the imaging element, the observation light incident on the imaging element is photoelectrically converted, such that an image signal corresponding to the observation light is generated. The image signal generated by the imaging unit 10112 is provided to the image processing unit 10113.

The image processing unit 10113 includes a processor such as a central processing unit (CPU) or a graphics processing unit (GPU) and performs various signal processing on the image signal generated by the imaging unit 10112. The image processing unit 10113 provides the image signal on which the signal processing is performed, as RAW data to the wireless communication unit 10114.

The wireless communication unit 10114 performs predetermined processing such as modulation processing on the image signal on which the signal processing is performed by the image processing unit 10113, and transmits the image signal on which the predetermined processing is performed to the external control device 10200 through an antenna 10114A. Furthermore, the wireless communication unit 10114 receives a control signal related to drive control of the capsule type endoscope 10100 from the external control device 10200 through the antenna 10114A. The wireless communication unit 10114 provides the control signal received from the external control device 10200 to the control unit 10117.

The power feeding unit 10115 includes an antenna coil for receiving power, a power regeneration circuit regenerating power from a current generated in the antenna coil, a booster circuit, and the like. The power feeding unit 10115 generates power using the principle of so-called contactless charging.

The power supply unit 10116 includes a secondary battery, and stores the power generated by the power feeding unit 10115. Illustration of an arrow or the like indicating a supply destination of the power from the power supply unit 10116 is omitted in FIG. 16 in order to avoid complication of the drawing, but the power stored in the power supply unit 10116 can be supplied to the light source unit 10111, the imaging unit 10112, the image processing unit 10113, the wireless communication unit 10114, and the control unit 10117 and be used to drive the light source unit 10111, the imaging unit 10112, the image processing unit 10113, the wireless communication unit 10114, and the control unit 10117.

The control unit 10117 includes a processor such as a CPU, and appropriately controls drive of the light source unit 10111, the imaging unit 10112, the image processing unit 10113, the wireless communication unit 10114, and the power feeding unit 10115 depending on a control signal transmitted from the external control device 10200.

The external control device 10200 includes a processor such as a CPU or a GPU, or a microcomputer, a control board or the like in which memory elements such as a processor and a memory are mixed with each other. The external control device 10200 controls an operation of the capsule type endoscope 10100 by transmitting the control signal to the control unit 10117 of the capsule type endoscope 10100 through an antenna 10200A. In the capsule type endoscope 10100, for example, an irradiation condition of the light to the observation target in the light source unit 10111 can be changed by the control signal from the external control device 10200. Furthermore, imaging conditions (for example, a frame rate, an exposure value or the like in the imaging unit 10112) can be changed by a control signal from the external control device 10200. Furthermore, contents of processing in the image processing unit 10113 and conditions (for example, transmission interval, number of transmission images and the like) under which the wireless communication unit 10114 transmits an image signal may be changed by a control signal from the external control device 10200.

Furthermore, the external control device 10200 performs various types of image processing on the image signal transmitted from the capsule type endoscope 10100, and generates image data for displaying the captured in-vivo image on the display device. As the image processing, for example, various signal processing such as development processing (demosaic processing), high image quality processing (band emphasis processing, super-resolution processing, noise reduction (NR) processing, and/or camera shake correction processing), and/or enlargement processing (electronic zoom processing), can be performed. The external control device 10200 controls drive of the display device to display the captured in-vivo image on the basis of the generated image data. Alternatively, the external control device 10200 may cause a recording device (not illustrated) to record the generated image data or cause a printing device (not illustrated) to print out the generated image data.

An example of the in-vivo information acquisition system to which the technology according to the present disclosure can be applied has been described hereinabove. The technology according to the present disclosure can be applied to the imaging unit 10112 among the configurations described above. Specifically, the imaging device 100 of FIG. 2 can be applied to the imaging unit 10112. By applying the technology according to the present disclosure to the imaging unit 10112, it is possible to reduce a height of the semiconductor package while maintaining a strength of the semiconductor chip, such that the capsule type endoscope 10100 can be further miniaturized to further reduce a burden on the patient.

<13. Application Example to Moving Body>

The technology according to the present disclosure (the present technology) can be applied to various products. For example, the technology according to the present disclosure may be realized as a device mounted in any one mobile object of a vehicle, an electric vehicle, a hybrid electric vehicle, a motorcycle, a bicycle, a personal mobility, an airplane, a drone, a ship, a robot, and the like.

Figure 17:
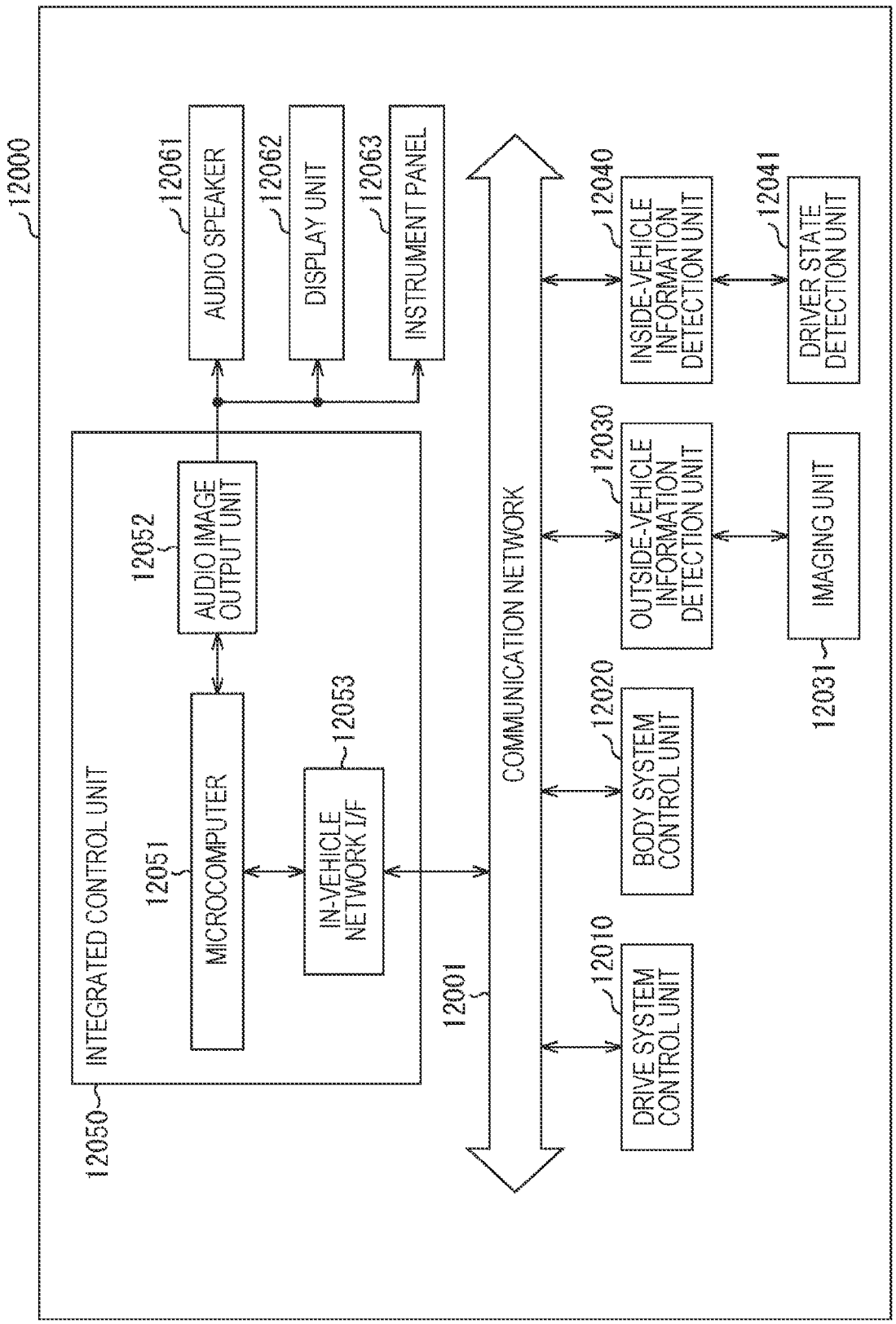
FIG. 17 is a block diagram illustrating an example of a schematic configuration of a vehicle control system.

FIG. 17 is a block diagram illustrating a schematic configuration example of a vehicle control system which is an example of a moving body control system to which the technology according to the present disclosure can be applied.

A vehicle control system 12000 includes a plurality of electronic control units connected to each other through a communication network 12001. In the example illustrated in FIG. 17, the vehicle control system 12000 includes a drive system control unit 12010, a body system control unit 12020, an outside-vehicle information detection unit 12030, an inside-vehicle information detection unit 12040, and an integrated control unit 12050. Furthermore, as a functional configuration of the integrated control unit 12050, a microcomputer 12051, an audio image output unit 12052, and an in-vehicle network interface (I/F) 12053 are illustrated.

The drive system control unit 12010 controls an operation of a device related to a drive system of a vehicle according to various programs. For example, the drive system control unit 12010 functions as a control device such as a driving force generation device for generating a driving force of the vehicle, such as an internal combustion engine or a drive motor, a driving force transfer mechanism for transferring the driving force to wheels, a steering mechanism for adjusting a steering angle of the vehicle, and a braking device for generating a braking force of the vehicle.

The body system control unit 12020 controls operations of various devices mounted on a vehicle body according to the various programs. For example, the body system control unit 12020 functions as a keyless entry system, a smart key system, a power window device, or a control device of various lamps such as a headlamp, a back lamp, a brake lamp, a blinker, or a fog lamp. In this case, the body system control unit 12020 can receive electric waves or signals of various switches transmitted from a portable device substituting for a key. The body system control unit 12020 receives inputs of these electric waves or signals, and controls a door lock device, a power window device, a lamp, and the like of the vehicle.

The outside-vehicle information detection unit 12030 detects information regarding the outside of the vehicle in which the vehicle control system 12000 is mounted. For example, an imaging unit 12031 is connected to the outside-vehicle information detection unit 12030. The outside-vehicle information detection unit 12030 causes the imaging unit 12031 to capture a vehicle external image, and receives the captured image. The outside-vehicle information detection unit 12030 may perform object detection processing or distance detection processing of a person, a vehicle, an obstacle, a sign, characters on a road surface, or the like on the basis of the received image.

The imaging unit 12031 is an optical sensor that receives light and outputs an electrical signal depending on an amount of received light. The imaging unit 12031 can output the electrical signal as an image or can output the electrical signal as measured distance information. Furthermore, the light received by the imaging unit 12031 may be visible light or may be non-visible light such as infrared light.

The inside-vehicle information detection unit 12040 detects information regarding the inside of the vehicle. For example, a driver state detection unit 12041 detecting a state of a driver is connected to the inside-vehicle information detection unit 12040. The driver state detection unit 12041 includes, for example, a camera imaging the driver, and the inside-vehicle information detection unit 12040 may calculate a fatigue degree or a concentration degree of the driver on the basis of detected information input from the driver state detection unit 12041 or may determine whether or not the driver is dozing.

The microcomputer 12051 can calculate a control target value of the driving force generation device, the steering mechanism, or the braking device on the basis of the information regarding the inside or the outside of the vehicle acquired by the outside-vehicle information detection unit 12030 or the inside-vehicle information detection unit 12040 and output a control command to the drive system control unit 12010. For example, the microcomputer 12051 can perform cooperation control for the purpose of realizing a function of an advanced driver assistance system (ADAS) including collision avoidance or shock mitigation of the vehicle, following traveling based on an inter-vehicle distance, vehicle speed maintenance traveling, collision warning of the vehicle, lane departure warning of the vehicle, and the like.

Furthermore, the microcomputer 12051 can perform cooperative control for the purpose of automatic driving or the like in which the vehicle autonomously travels without depending on a driver's operation by controlling the driving force generating device, the steering mechanism, the braking device, or the like, on the basis of the surrounding information of the vehicle acquired by the outside-vehicle information detection unit 12030 or the inside-vehicle information detection unit 12040.

Furthermore, the microcomputer 12051 can output a control command to the body system control unit 12020 on the basis of the information regarding the outside of the vehicle acquired by the outside-vehicle information detection unit 12030. For example, the microcomputer 12051 can perform cooperative control for the purpose of achieving antiglare such as switching a high beam into a low beam by controlling the headlamp depending on a position of the preceding vehicle or an oncoming vehicle detected by the outside-vehicle information detection unit 12030.

The audio image output unit 12052 transmits at least one of an audio output signal or an image output signal to an output device capable of visually or auditorily notifying a passenger or the outside of the vehicle of information. In the example of FIG. 17, an audio speaker 12061, a display unit 12062, and an instrument panel 12063 are illustrated as the output device. The display unit 12062 may include, for example, at least one of an on-board display or a head-up display.

Figure 18:
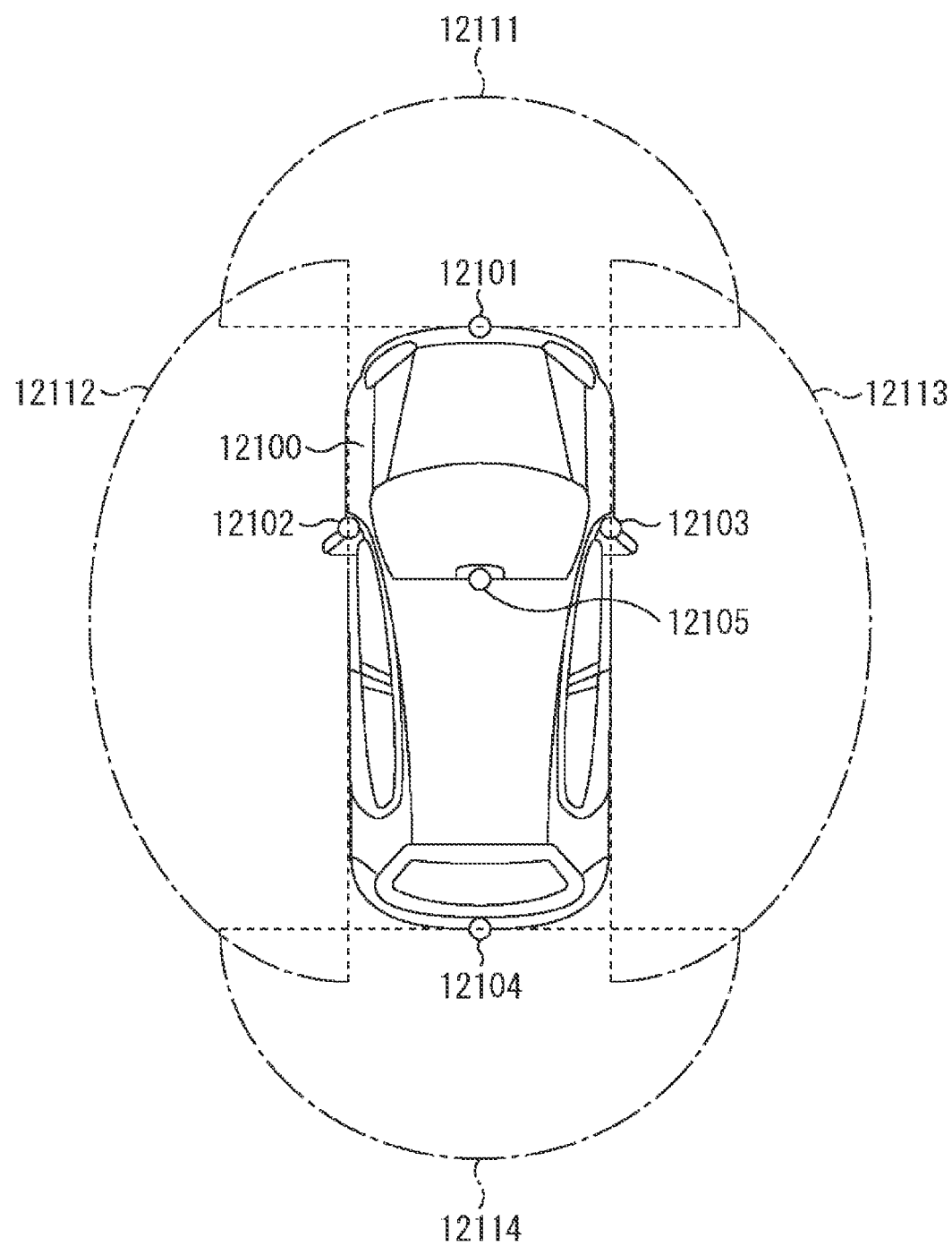
FIG. 18 is an explanatory view illustrating an example of installation positions of an outside-vehicle information detection unit and an imaging unit.

FIG. 18 is a view illustrating an example of an installation position of the imaging unit 12031.

In FIG. 18, a vehicle 12100 includes imaging units 12101, 12102, 12103, 12104, and 12105 as the imaging unit 12031.

The imaging units 12101, 12102, 12103, 12104, and 12105 are provided, for example, at positions such as a front nose, side mirrors, a rear bumper, a back door, and an upper portion of a windshield of a vehicle interior, of the vehicle 12100. The imaging unit 12101 included in the front nose and the imaging unit 12105 included in the upper portion of the windshield of the vehicle interior mainly acquire images of a region in front of the vehicle 12100. The imaging units 12102 and 12103 included in the side mirrors mainly acquire images side regions of the vehicle 12100. The imaging units 12104 included in the rear bumper or the back door mainly acquire an image of a region behind the vehicle 12100. The images of the region in front of the vehicle acquired by the imaging units 12101 and 12105 are mainly used to detect the preceding vehicle, a pedestrian, an obstacle, a traffic light, a traffic sign, a lane, or the like.

Note that FIG. 18 illustrates an example of imaging ranges of the imaging units 12101 to 12104. An imaging range 12111 indicates an imaging range of the imaging unit 12101 provided on the front nose, imaging ranges 12112 and 12113 indicate imaging ranges of the imaging units 12102 and 12103 provided on the side mirrors, respectively, and an imaging range 12114 indicates an imaging range of the imaging unit 12104 provided in the rear bumper or the back door. For example, by overlaying image data captured by the imaging units 12101 to 12104 with each other, a bird's eye view image of the vehicle 12100 viewed from above can be obtained.

At least one of the imaging units 12101 to 12104 may have a function of acquiring distance information. For example, at least one of the imaging units 12101 to 12104 may be a stereo camera including a plurality of imaging elements or may be an imaging element having pixels for detecting a phase difference.

For example, the microcomputer 12051 can extract, in particular, a three-dimensional object that is the closest three-dimensional object on a traveling road of the vehicle 12100 and travels at a predetermined speed (for example, 0 km/h or more) in substantially the same direction that of the vehicle 12100 as the preceding vehicle by calculating a distance to each three-dimensional object in the imaging ranges 12111 to 12114 and a temporal change (a relative velocity to the vehicle 12100) in this distance on the basis of the distance information acquired from the imaging units 12101 to 12104. Moreover, the microcomputer 12051 can set an inter-vehicle distance to be secured in advance in front of the preceding vehicle and perform automatic brake control (including following stop control), automatic acceleration control (including following start control), and the like. As described above, it is possible to perform the cooperative control for the purpose of the automatic driving or the like in which the vehicle autonomously travels without depending on the driver's operation.

For example, the microcomputer 12051 can classify and extract three-dimensional object data related to the three-dimensional objects into other three-dimensional objects such as a two-wheeled vehicle, an ordinary vehicle, a large vehicle, a pedestrian, and a telephone pole, on the basis of the distance information acquired from the imaging units 12101 to 12104, and use the three-dimensional object data for automatic avoidance of an obstacle. For example, the microcomputer 12051 identifies obstacles around the vehicle 12100 as obstacles visible to the driver of the vehicle 12100 and obstacles invisible to the driver of the vehicle 12100. Then, the microcomputer 12051 can perform driving support for collision avoidance by determining a collision risk indicating a risk of collision with each obstacle and outputting a warning to the driver through the audio speaker 12061 or the display unit 12062 or performing forced deceleration or avoidance steering through the drive system control unit 12010 in a situation where the collision risk is a set value or more, so there is a possibility of collision.

At least one of the imaging units 12101 to 12104 may be an infrared camera detecting infrared light. For example, the microcomputer 12051 can recognize a pedestrian by determining whether or not the pedestrian is present in the images captured of the imaging units 12101 to 12104. Such recognition of the pedestrian is performed by, for example, a procedure for extracting feature points in images captured by the imaging units 12101 to 12104 as the infrared camera and a procedure of performing pattern matching processing on a series of feature points indicating an outline of an object to distinguish whether or not the object is the pedestrian. When the microcomputer 12051 determines that the pedestrian is present in the images captured by the imaging units 12101 to 12104 and recognizes the pedestrian, the audio image output unit 12052 controls the display unit 12062 to superimpose and display a rectangular outline for emphasizing the recognized pedestrian. Furthermore, the audio image output unit 12052 may control the display unit 12062 to display an icon or the like indicating the pedestrian on a desired position.

An example of the vehicle control system to which the technology according to the present disclosure can be applied has been described hereinabove. The technology according to the present disclosure can be applied to the imaging unit 12031 among the configurations described above. Specifically, the imaging device 100 of FIG. 2 can be applied to the imaging unit 12031. By applying the technology according to the present disclosure to the imaging unit 12031, it is possible to reduce a height of the semiconductor package while maintaining a strength of the semiconductor chip, such that the imaging unit 12031 can be further miniaturized to increase a degree of freedom of an installation position of the imaging unit 12031.

Note that the embodiments of the present technology are not limited to the embodiments described above, and various modifications can be made without departing from the scope of the present technology. For example, at least two or more of the first to eighth embodiments can be combined with each other.

Furthermore, the present technology can adopt the following configurations.

(1)

An imaging device including:
- a first substrate having a pixel region in which pixels are two-dimensionally arranged, the pixels performing photoelectric conversion of light; and
- a second substrate in which a through silicon via is formed,
- in which a dug portion is formed in a back surface of the second substrate opposite to an incident side of light of the second substrate, and
- a redistribution layer (RDL) connected to a back surface of the first substrate is formed in the dug portion.

(2)

The imaging device according to the above (1), in which the second substrate has a region of a frame shape when viewed from a back surface side due to the formation of the dug portion.

(3)

The imaging device according to the above (1) or (2), in which the dug portion has a forward tapered shape.

(4)

The imaging device according to any one of the above (1) to (3), in which a solder ball is mounted on the redistribution layer, and
- a solder mask is embedded and planarized in the dug portion.

(5)

The imaging device according to the above (4), in which the solder ball protrudes with respect to a surface of the solder mask.

(6)

The imaging device according to the above (4), in which the solder ball is planarized so as to be flush with a surface of the solder mask.

(7)

The imaging device according to the above (4), in which a surface of the solder ball, a surface of the solder mask, and a surface of the region of the frame shape are planarized so as to be flush with one another.

(8)

The imaging device according to any one of the above (1) to (3), in which a land grid array (LGA) is formed on the redistribution layer.

(9)

The imaging device according to any one of the above (1) to (3), in which the redistribution layer has a multilayer redistribution layer (RDL) structure.

(10)

The imaging device according to the above (2), in which the second substrate has a region having a large film thickness in addition to the region of the frame shape.

(11)

The imaging device according to the above (10), in which the first substrate is an image sensor, and
- the second substrate has the region having the large film thickness at a position corresponding to a central portion of the image sensor.

(12)

The imaging device according to any one of the above (1) to (11), further including:
- a transparent member through which light is incident; and
- an adhesive which bonds the transparent member and the first substrate to each other, in which the pixels two-dimensionally arranged in the pixel region perform the photoelectric conversion of the light incident through the transparent member.

(13)

The imaging device according to the above (12), in which the imaging device is configured as a wafer level chip size package (WCSP).

(14)

The imaging device according to the above (2), in which the second substrate includes silicon (Si).

(15)

The imaging device according to the above (14), in which the region of the frame shape includes a scribe region.

(16)

An electronic apparatus including an imaging device,
- in which the imaging device includes:
- a first substrate having a pixel region in which pixels are two-dimensionally arranged,
- the pixels performing photoelectric conversion of light; and
- a second substrate in which a through silicon via is formed,
- a dug portion being formed in a back surface of the second substrate opposite to an incident side of light of the second substrate, and
- a redistribution layer (RDL) connected to a back surface of the first substrate being formed in the dug portion.

(17)

A method of manufacturing an imaging device, including:
- a first step of forming a dug portion in a back surface of a second substrate opposite to an incident side of light of the second substrate in which a through silicon via is formed, in a first substrate having a pixel region in which pixels are two-dimensionally arranged and the second substrate stacked on the first substrate, the pixels performing photoelectric conversion of light; and
- a second step of forming a redistribution layer (RDL) in the dug portion, the redistribution layer (RDL) being connected to a back surface of the first substrate.

(18)

The method of manufacturing an imaging device according to the above (17), further including:
- a third step of embedding a solder mask in the dug portion;
- a fourth step of patterning the solder mask embedded in the dug portion to define a position at which a solder ball is to be mounted; and
- a fifth step of mounting the solder ball on the redistribution layer according to the defined position.

(19)

The method of manufacturing an imaging device according to the above (18), further including, after the third step and before the fourth step, a sixth step of planarizing the solder mask.

(20)
The method of manufacturing an imaging device according to the above (18), further including, after the fifth step, a sixth step of planarizing the solder mask and the solder ball.

REFERENCE SIGNS LIST 100, 100A to 100G Imaging device
111 Transparent member
112 Adhesive
113 On-chip lens
114 First substrate
115, 115A to 115G Second substrate
116, 116A to 116G TSV/RDL wiring
117, 117A to 117G Solder mask
118, 118A to 118D Solder ball
121 Dug portion
122 Frame portion
131 Scribe Portion
1000 Electronic Apparatus
1001 Semiconductor package
10112 Imaging unit
12031 Imaging unit

The invention claimed is:

1. An imaging device, comprising:
a plurality of pixels configured to execute photoelectric conversion of light;
a first substrate having a pixel region, wherein the pixel region includes the plurality of pixels in a two-dimensional arrangement;
a second substrate;
a through silicon via in the second substrate, wherein the through silicon via penetrates the second substrate from a dug portion to a back surface of the first substrate;
the dug portion in a back surface of the second substrate, wherein a side surface of the dug portion has a tapered shape, and
the back surface of the second substrate is opposite to a light incident side of the second substrate;
a redistribution layer in the dug portion, wherein
the redistribution layer is connected to the back surface of the first substrate, and
the back surface of the first substrate is opposite to a light incident side of the first substrate; and
a solder ball in the dug portion, wherein the solder ball is on the redistribution layer.

2. The imaging device according to claim 1, wherein
the second substrate has a first region, and
the first region has a frame shape from the back surface of the second substrate.

3. The imaging device according to claim 2, further comprising a solder mask that is embedded and planarized in the dug portion.

4. The imaging device according to claim 3, wherein the solder ball protrudes with respect to a surface of the solder mask.

5. The imaging device according to claim 3, wherein the solder ball is flush with a surface of the solder mask.

6. The imaging device according to claim 3, wherein a surface of the solder ball, a surface of the solder mask, and a surface of the first region of the second substrate are planarized.

7. The imaging device according to claim 2, wherein
the second substrate has a second region, and
a film thickness of the second region is larger than a film thickness of the first region.

8. The imaging device according to claim 7, wherein
the first substrate is an image sensor, and
the second region of the second substrate is at a position that corresponds to a central portion of the image sensor.

9. The imaging device according to claim 2, wherein the second substrate includes silicon (Si).

10. The imaging device according to claim 9, wherein the first region of the frame shape includes a scribe region.

11. The imaging device according to claim 1, further comprising:
a transparent member through which the light is incident; and
an adhesive which bonds the transparent member with the first substrate, wherein the plurality of pixels is further configured to execute the photoelectric conversion of the light incident through the transparent member.

12. The imaging device according to claim 11, wherein the imaging device is a wafer level chip size package (WCSP).

13. An electronic apparatus, comprising:
an imaging device, wherein the imaging device includes:
a plurality of pixels configured to execute photoelectric conversion of light;
a first substrate having a pixel region, wherein the pixel region includes the plurality of pixels in a two-dimensional arrangement;
a second substrate;
a through silicon via in the second substrate, wherein the through silicon via penetrates the second substrate from a dug portion to a back surface of the first substrate;
the dug portion in a back surface of the second substrate, wherein
a side surface of the dug portion has a tapered shape, and
the back surface of the second substrate is opposite to a light incident side of the second substrate;
a redistribution layer in the dug portion, wherein
the redistribution layer is connected to the back surface of the first substrate, and
the back surface of the first substrate is opposite to a light incident side of the first substrate; and
a solder ball in the dug portion, wherein the solder ball is on the redistribution layer.

* * * * *